(12) United States Patent
Yin et al.

(10) Patent No.: US 11,603,416 B2
(45) Date of Patent: Mar. 14, 2023

(54) METHOD FOR PREPARATION OF DERIVATIVES OF GRAM-POSITIVE BACTERIA SURFACE CAPSULAR POLYSACCHARIDE

(71) Applicant: Jiangnan University, Wuxi (CN)

(72) Inventors: Jian Yin, Wuxi (CN); Jing Hu, Wuxi (CN); Juntao Cai, Wuxi (CN)

(73) Assignee: Jiangnan University, Wuxi (CN)

( * ) Notice: Subject to any disclaimer, the term of this patent is extended or adjusted under 35 U.S.C. 154(b) by 115 days.

(21) Appl. No.: 17/004,067

(22) Filed: Aug. 27, 2020

(65) Prior Publication Data
US 2021/0002388 A1 Jan. 7, 2021

Related U.S. Application Data

(63) Continuation of application No. PCT/CN2019/077636, filed on Mar. 11, 2019.

(30) Foreign Application Priority Data

Mar. 20, 2018 (CN) .................. 201810229446.X

(51) Int. Cl.
| | | |
|---|---|---|
| *C08B 37/00* | (2006.01) | |
| *C07H 1/00* | (2006.01) | |
| *C07H 3/04* | (2006.01) | |
| *C07H 3/06* | (2006.01) | |
| *C07H 15/26* | (2006.01) | |
| *C07H 5/10* | (2006.01) | |
| *C07H 9/04* | (2006.01) | |

(52) U.S. Cl.
CPC ............. *C08B 37/006* (2013.01); *C07H 1/00* (2013.01); *C07H 3/04* (2013.01); *C07H 3/06* (2013.01); *C07H 5/10* (2013.01); *C07H 9/04* (2013.01); *C07H 15/26* (2013.01)

(58) Field of Classification Search
None
See application file for complete search history.

(56) References Cited

FOREIGN PATENT DOCUMENTS

CN 108329362 A 7/2018

OTHER PUBLICATIONS

Schuele et al., Tetrahedron, vol. 79, No. 23, Dec. 1996, pp. 9022-9029 (Year: 1996).*
PCT/CN2019/077636 ISA210 ISR Mail Date Jun. 17, 2019.
Schuele. G. et al. "Schuele. G. et al .• Efficient Convergent Block Synthesis of a Pyruvated Tetrasaccharide 5-Aminopentyl Glycoside Related to *Streptococcus pneumoniae* Type 27" Tetrahedron, vol. 79, No. (23), Dec. 31, 1996 (Dec. 31, 1996),pp. 9022-9029.
Suzuki, K. et al. "High-Yielding and Controlled Dissociation of Glycosides Producing B- and C-Ion Species under Collision-Induced Dissociation MS/MS Conditions and Use in Structural Determination" Analytical Chemistry, vol. 79, No. (23), Dec. 1, 2007 (Dec. 1, 2007), pp. 9022-9029.
Deng, Kai et al. "Encoding Substrates with Mass Tags to Resolve Stereospecific Reactions Using Nimzyme" Rapid Commun. Mass Spectrum., vol. vol. 26, Dec. 31, 2012 (Dec. 31, 2012),pp. 611-615.
Muller. D. et al. "Chemical Synthesis of Globotriose and Galabiose: Relative Stabilities of Their Complexes with *Escherichia coli* Shiga-Like Toxin-1 as Determined by Denaturation-Titration with Guanidinium Chloride" J. Chem. Soc.Perkin Transactions 1: Organic and Bio-Organic Chemistry, No. No. 15, Jan. 1, 1998 (Jan. 1, 1998), pp. 2287-2294.
Anish, C. et al. "Immunogenicity and Diagnostic Potential of Synthetic Antigenic Cell Surface Glycans of Leishmania" ACS Chem. Biol., vol. vol. 8, Sep. 4, 2013 (Sep. 4, 2013), pp. 2412-2422.

\* cited by examiner

*Primary Examiner* — Traviss C McIntosh, III
(74) *Attorney, Agent, or Firm* — IPro, PLLC

(57) ABSTRACT

The present disclosure discloses a method for preparation of derivatives of gram-positive bacteria surface capsular polysaccharide, and belongs to the field of carbohydrate chemistry. The present disclosure takes glucose as a glycosyl donor to obtain a target β-glucosidic bond, then successfully synthesizes a disaccharide building block through a method of redox of a glucose C-2 site, and then takes the disaccharide building block as a repeat unit to synthesize a target oligosaccharide structure such as a derivative [→3)-α-D-Manp-(1→4)-β-D-Rhap-(1→]$_5$-Linker of gram-positive bacteria cell wall capsular polysaccharide. A reduction end of decose is linked with a linker to be linked with a protein to make glycoconjugates for immunological studies. The method provided by the present disclosure is simple, time-saving, labor-saving and low-cost, and the resultant derivatives of the gram-positive bacteria surface capsular polysaccharide may be used for development and preparation of medicine related to autism.

17 Claims, 6 Drawing Sheets

METHOD FOR PREPARATION OF DERIVATIVES OF GRAM-POSITIVE BACTERIA SURFACE CAPSULAR POLYSACCHARIDE

TECHNICAL FIELD

The present disclosure relates to a method for preparation of derivatives of gram-positive bacteria surface capsular polysaccharide, and belongs to the field of carbohydrate chemistry.

BACKGROUND

Autism, also known as autistic disorder, was first discovered by American psychiatrist Leo Kanner in clinical medicine and the concept was proposed in the late 1930s. The main manifestations of autism are socialization disorder, language communication disorder and behavioral habit disorder of children. According to current international commonly referred standards, 1 in 160 children suffers from autism. The number of children with autism in China was reckoned at about 1.64 million in 2012 on the basis, and has already reached one thousandth of the population with an annual growing rate of 10% to 17%. Around the world, the autism has received increasing concern and attention. From 2008, the United Nations General Assembly designated April 2nd as "World Autism Awareness Day" for encouraging organization of World Autism Awareness Day activities in an appropriate manner every year in order to raise public awareness of autism, and measure adoption at the family level is included so as to raise awareness of autistic children throughout the society.

*C. bolteae* is an anaerobic gram-positive bacterium with an optimal survival environmental temperature of 37° C., which is exactly the normal temperature of a human body. Massive reproduction of *C. bolteae* in intestinal canals can lead to a higher proportion of gastrointestinal discomfort including constipation and diarrhea, the influence of the discomfort on behavioral habits of autistic patients may be related to short chain fatty acids, such as propionic acid (PPA), generated by metabolism of carbohydrates through bacteria, and the PPA metabolite can weaken gastric motility and increase the frequency of intestinal canal contractions, which may be directly related to gastrointestinal discomfort of patients with ASD. In the treatment of children with severe ASD accompanied by chronic and persistent diarrhea through oral administration of vancomycin (a glycopeptide antibiotic used to prevent and treat infections caused by the gram-positive bacteria), researchers found that the autism symptoms of 80% of child patients have been relieved for a short time, but the effect will disappear once the drug is discontinued, which shows that the vancomycin only inhibits but not eliminate the dysbacteriosis, and also shows that inhibition of growth of the corresponding gram-positive bacteria can indeed relieve the autism symptoms. However, long-term administration of the vancomycin may cause the bacteria to generate drug resistance, so there is an urgent need to research and develop other treatment solutions that can control the reproduction of major pathogenic bacteria such as *C. bolteae* in the intestinal canals.

SUMMARY

At present, there are no vaccines on the market that can prevent *C. bolteae* infection or treat *C. bolteae*. Carbohydrate vaccines, as a new target molecule for the development of the vaccines, get more and more attention from scientists, and polysaccharide structures on surfaces of bacteria tend to play an important role in pathogenicity of the bacteria and immunity recognition in a human body. So far, there is no research on a chemically synthesized *C. bolteae* cell wall capsular polysaccharide as a vaccine, and a biological method for extracting and purifying the polysaccharide structures mainly has the following disadvantages: 1) an extraction and purification process consumes a long time, and is high in cost, and the amount of extraction each time is relatively small; and 2) it is difficult to obtain a product with high purity and single structure, and impurities in the product may bring a series of problems and difficulties to subsequent vaccine preparation. Preparation of oligo/polysaccharide structures through chemical synthesis can achieve large-scale preparation of products, and a synthesized product has a single structure and is free of impurities, which solves the main problems in biological-method purification. Therefore, synthesis of *C. bolteae* surface oligo/polysaccharides through a chemical method has great significance to development of a *C. bolteae* vaccine.

The present disclosure mainly aims to prepare a vaccine capable of reducing gastrointestinal irritation of bacteria on autistic patients, focuses on an intestinal canal gram-positive bacterium *Clostridium bolteae* related to tardive autism, takes a cell wall capsular polysaccharide structure on a surface of its cell wall as the research object, and designs and uses a chemical method to synthesize the polysaccharide structure and prepare sugar-protein conjugates for subsequent immunological research on the synthesized conjugates in mice. On the one hand, it is hoped that this cell wall capsular polysaccharide (CPS) structure can be applied to clinical diagnosis of patients so as to establish corresponding treatment solutions; on the other hand, it is hoped to use this polysaccharide to develop vaccines to alleviate, through controlling the number of *C. bolteae* floras in the intestinal canals of children with autism, suffering of the autistic patients, prevent symptoms associated with the tardive autism, and help them more effectively receive rehabilitation training.

*C. bolteae* surface capsular polysaccharide is composed of a repeat disaccharide fragment, the disaccharide fragment is composed of a D-mannose and a D-rhamnose, and its structure can be characterized as [→3)-α-D-Manp-(1→4)-β-D-Rhap-(1→]n. According to the analysis of mass spectrometry data, this polysaccharide structure is composed of 9 repeat fragments (n=9).

The present disclosure designs to construct a synthetic carbohydrate antigenic reservoir containing one disaccharide fragment to five disaccharide fragments (namely one decose) by linking disaccharide units one by one through glycosylation reaction to synthesize oligosaccharide structures of different lengths, with one disaccharide fragment as a synthesis unit. Then, the synthesized oligosaccharide structures of different lengths are further conjugated with carrier proteins for the purpose of carrying out subsequent immunological research. Therefore, in a chemical synthesis process, it is necessary to introduce linkers into the target oligosaccharide structures. The present disclosure selects an aminopentyl linker ($NH_2$—$(CH_2)_5$—) for modifying an oligosaccharide reducing end.

A first problem solved by the present disclosure is synthesis of β-D-rhamnoside glycosidic bonds in a *C. bolteae* capsular polysaccharide structure. D-rhamnose, namely 6-deoxy-D-mannose, easily forms a dominant α-D-pyran rhamnoside glycosidic bond during synthesis of the glycosidic bond irrespective of end group effects or spatial effects; and because a C-2 site may has a neighboring group participating effect, 1,2-trans-glycosidic bonds may be stereoselectively generated, and the α-D-pyran rhamnoside glycosidic bond may also be easily obtained. The synthesis of β-D-pyran mannoside bonds has always been a research hotspot in glycosynthetic chemistry, and is also one of major challenges in carbohydrate chemistry. This glycosidic bond can be considered as one of the end group glycosidic bonds which are the most difficult to construct. The present disclosure adopts a C-2 site redox method to synthesize the target oligosaccharide structure.

A method for synthesizing the β-D-rhamnoside glycosidic bonds provided by the present disclosure includes: first synthesizing 6-deoxy-D-glucopyranoside, protecting a C-2 site of the target compound with an acyl protecting group, utilizing a neighboring group participating effect to stereoselectively generate β-D-glucopyranoside, then selectively removing the acyl protecting group at the C-2 site of glucose, and using a sulfonyl group or the like at the C-2 site to transpose an equatorial bond at the C-2 site to an axial bond through $SN_2$ mechanism nucleophilic substitution, so that a β-D-pyran rhamnoside glycoside can be obtained; or utilizing a redox method to first oxidize the C-2 site to a ketone, and then performing reduction by utilizing a reducing agent such as lithium aluminum hydride or sodium borohydride to obtain a compound with a C-2 site being an axial bond, namely to obtain the β-D-pyran rhamnoside glycoside.

Based on the method for synthesizing the β-D-rhamnoside glycosidic bonds, the present disclosure obtains the synthetic carbohydrate reservoir containing two disaccharide fragments (namely a disaccharide) to five disaccharide fragments (namely the decose).

A structure of the decose is shown in formula I:

Formula I 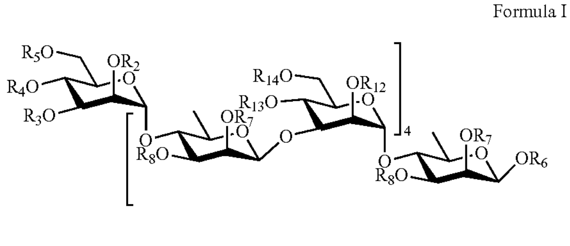 $R_6$ is an aminolink [—$(CH_2)_n$—N—$Y_1Y_2$, n=1 to 10], and is used to be linked with a protein to prepare a glycoprotein for immunology research; n represents that the aminolink may have different carbon chain lengths, $Y_1$ and $Y_2$ are protecting groups for amino, $Y_{1/2}$ is H or benzyl (Bn), and $Y_{2/1}$ is H or benzyloxycarbonyl (Cbz); $R_2$, $R_3$, $R_4$ and $R_5$ groups are H, or acetyl (Ac), or benzoyl (Bz), or pivalyl (Piv), or chloroacetyl (ClAc), or levulinic acyl (Lev), or allyloxycarbonyl (Alloc), or benzyl (Bn), or 2-menaphthyl (Nap), or allyl (All), or benzylidene acetal, or isopropylidene ketal or the like; $R_7$ and $R_{12}$ groups are H, or acetyl (Ac), or benzoyl (Bz), or pivalyl (Piv), or chloroacetyl (ClAc), or levulinic acyl (Lev), or allyloxycarbonyl (Alloc) or the like, and the $R_8$ group is H, or benzyl (Bn), or allyl (All) or the like; and $R_{13}$ and $R_{14}$ groups are H, or benzyl (Bn), or 2-menaphthyl (Nap), or allyl (All), or benzylidene acetal, or isopropylidene ketal or the like.

A structure of the disaccharide is shown in the following formula:

wherein $R_2$, $R_3$, $R_4$, $R_5$, $R_6$, $R_7$ and $R_8$ refer to formula I.

A structure of a trisaccharide is shown in the following formula:

n = 1 wherein $R_{12}$, $R_{13}$, $R_{14}$, $R_6$, $R_7$ and $R_8$ refer to formula I.

A structure of a tetrasaccharide is shown in the following formula:

n = 1 wherein $R_2$, $R_3$, $R_4$, $R_5$, $R_6$, $R_7$, $R_8$, $R_{12}$, $R_{13}$ and $R_{14}$ refer to formula I.

A structure of a pentaose is shown in the following formula:

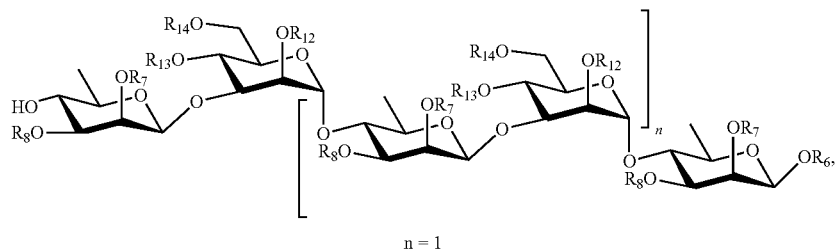

n = 1 wherein $R_6$, $R_7$, $R_8$, $R_{12}$, $R_{13}$ and $R_{14}$ refer to formula I.

A structure of a hexaose is shown in the following formula:

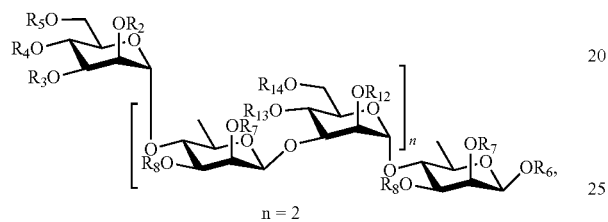

n = 2 wherein $R_2$, $R_3$, $R_4$, $R_5$, $R_{12}$, $R_{13}$, $R_{14}$, $R_6$, $R_7$ and $R_8$ refer to formula I.

A structure of a heptaose is shown in the following formula:

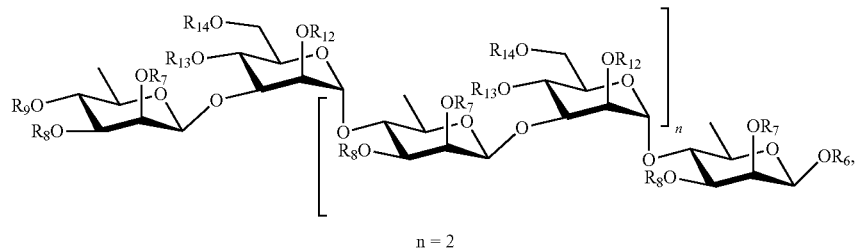

n = 2 wherein $R_{12}$, $R_{13}$, $R_{14}$, $R_6$, $R_7$, $R_8$ and $R_9$ refer to formula I.

A structure of an octaose is shown in the following formula:

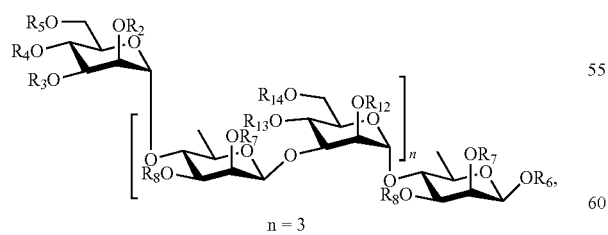

n = 3 wherein $R_2$, $R_3$, $R_4$, $R_5$, $R_{12}$, $R_{13}$, $R_{14}$, $R_6$, $R_7$ and $R_8$ refer to formula I.

A structure of a nonose is shown in the following formula:

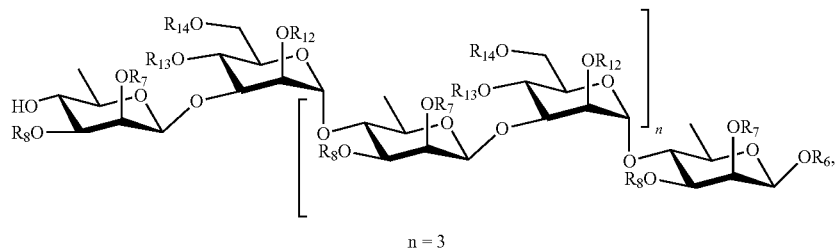

n = 3 wherein $R_{12}$, $R_{13}$, $R_{14}$, $R_6$, $R_7$ and $R_8$ refer to formula I.

Synthesis of the target molecule decose specifically includes the following steps:

Step I, synthesis of a mannose carbohydrate building block 1:

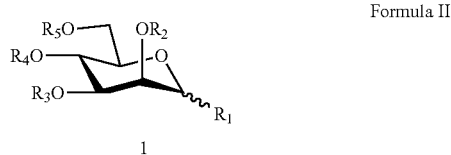

Formula II

The carbohydrate building block 1 is shown in formula II, an end group site $R_1$ thereof is a glycosyl donor, and may be halogenated sugar, glucosinolate, trichloroacetimidate glycoside, phosphate glycoside, sulfoxide glycoside, N-phenyl trifluoroacetimidate glycoside and the like, for example, the $R_1$ group is fluorine (F), or chlorine (Cl), or bromine (Br), or trichloroacetimidate ($CCl_3C(=NH)O—$), or N-phenyl trifluoroacetimidate glycoside ($CF_3C(=NPh)O—$), or ethyl sulfenyl (SEt), or thiophenyl (SPh), or paratoluene sulfenyl (STol), or ethyl sulfenyl (SEt), or dibutyl phosphonic acid groups ($—P(=O)—(OBu)_2$) or the like; the end group site is of an α or β configuration; and the remaining substituents $R_n$ refer to formula I.

Step II, synthesis of a rhamnose building block 2:

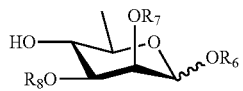

The carbohydrate building block 2 is shown in formula III, and the substituents $R_n$ refer to formula I.

Step III, synthesis of a rhamnose carbohydrate building block 4:

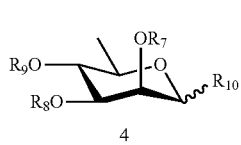

Formula IV

The carbohydrate building block 4 is shown in formula IV, an end group site $R_{10}$ thereof is a glycosyl donor, and may be halogenated sugar, glucosinolate, trichloroacetimidate glycoside, phosphate glycoside, sulfoxide glycoside, N-phenyl trifluoroacetimidate glycoside or the like, for example, the $R_{10}$ group is fluorine (F), or chlorine (Cl), or bromine (Br), or trichloroacetimidate ($CCl_3C(=NH)O—$), or N-phenyl trifluoroacetimidate glycoside ($CF_3C(=NPh)O—$), or ethyl sulfenyl (SEt), or thiophenyl (SPh), or paratoluene sulfenyl (STol), or ethyl sulfenyl (SEt), or dibutyl phosphonic acid groups ($—P(=O)—(OBu)_2$) or the like; the end group site is of an α or β configuration; the $R_9$ group is 2-menaphthyl (Nap), and the remaining substituents $R_n$ refer to formula I.

Step IV, synthesis of a mannose carbohydrate building block 5:

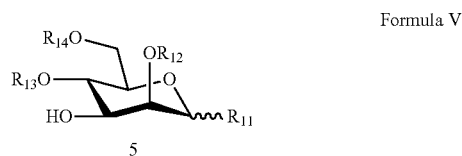

Formula V

The carbohydrate building block 5 is shown in formula V, an end group site $R_{10}$ thereof is a glycosyl donor, and may be halogenated sugar, or glucosinolate, or trichloroacetimidate glycoside, or phosphate glycoside, or sulfoxide glycoside, or N-phenyl trifluoroacetimidate glycoside or the like, for example, the $R_{11}$ group is fluorine (F), or chlorine (Cl), or bromine (Br), or trichloroacetimidate ($CCl_3C(=NH)O—$), or N-phenyl trifluoroacetimidate glycoside ($CF_3C(=NPh)O—$), or ethyl sulfenyl (SEt), or thiophenyl (SPh), or paratoluene sulfenyl (STol), or ethyl sulfenyl (SEt), or dibutyl phosphonic acid groups ($—P(=O)—(OBu)_2$) or the like; the end group site is of an α or β configuration; and the remaining substituents $R_n$ refer to formula I.

Step V, synthesis of a mannose carbohydrate building block 6:

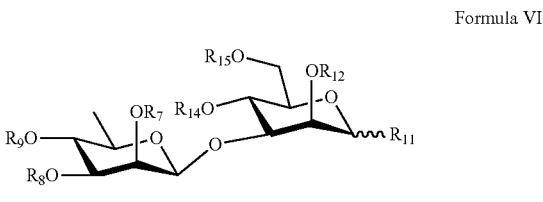

Formula VI

The carbohydrate building block 6 is shown in formula VI, and the substituents $R_n$ refer to formula IV and formula V.

Step VI, as in formula VII, an assembly of autism-associated gram-positive bacteria (*Clostridium bolteae*) surface capsular polysaccharide oligosaccharide fragments such as a disaccharide, a trisaccharide, a tetrasaccharide, a pentaose, a hexaose, a heptaose, an octaose, a nonose and a decose: by utilizing the carbohydrate building blocks 1, 2, 4, 5 and 6, reaction steps of the assembly of oligosaccharides are shown below:

(1) taking 3 mol of the carbohydrate building block 1 as a glycosyl donor, taking 1 mol of the carbohydrate building block 2 as a glycosyl receptor, dissolving the glycosyl donor and the glycosyl receptor in dry methylene dichloride, adding a 4 Å molecular sieve, then performing lewis acid catalysis, and stirring at a certain temperature for reaction for 2 to 10 hours to prepare a 1,4-α-linked target disaccharide fragment 3;

(2) taking 1 mol of the carbohydrate building block 4 as a glycosyl donor, taking 1.5 mol of the carbohydrate building block 5 as a glycosyl receptor, dissolving the glycosyl donor and the glycosyl receptor in dry methylene dichloride, adding an activated 4 Å molecular sieve, then performing lewis acid catalysis, and stirring at a certain temperature for reaction for 2 to 10 hours to prepare a 1,3-β-linked disaccharide building block 6;

(3) taking 1.5 mol of the disaccharide building block 6 as a glycosyl donor, taking 1 mol of the carbohydrate building block 2 as a glycosyl receptor, dissolving the glycosyl donor and the glycosyl receptor in methylene dichloride, then performing lewis acid catalysis, and stirring at a certain temperature for reaction for 2 to 10 hours to prepare a trisaccharide fragment 7; selectively eliminating $R_9$ to obtain a trisaccharide building block 8 with a free hydroxyl group at the C-4 site, taking 3 mol of the carbohydrate building block 1 as a glycosyl donor, taking 1 mol of the trisaccharide building block 8 as a glycosyl receptor, dissolving the glycosyl donor and the glycosyl receptor in dry methylene dichloride, adding a 4 Å molecular sieve, then performing lewis acid catalysis, and stirring at a certain temperature for reaction for 2 to 10 hours to prepare a target tetrasaccharide fragment 9;

(4) taking 1.5 mol of the disaccharide building block 6 as a glycosyl donor, taking 1 mol of the carbohydrate building block 8 as a glycosyl receptor, dissolving the glycosyl donor and the glycosyl receptor in methylene dichloride, then performing lewis acid catalysis, and stirring at a certain temperature for reaction for 2 to 10 hours to prepare a pentaose fragment 10; selectively eliminating $R_9$ to obtain a pentaose building block 11 with a free hydroxyl group at the C-4 site, taking 3 mol of the carbohydrate building block 1 as a glycosyl donor, taking 1 mol of the pentaose building block 11 as a glycosyl receptor, dissolving the glycosyl donor and the glycosyl receptor in dry methylene dichloride, adding a 4 Å molecular sieve, then performing lewis acid catalysis, and stirring at a certain temperature for reaction for 2 to 10 hours to prepare a target hexaose fragment 12;

(5) taking 1.5 mol of the disaccharide building block 6 as a glycosyl donor, taking 1 mol of the carbohydrate building block 11 as a glycosyl receptor, dissolving the glycosyl donor and the glycosyl receptor in methylene dichloride, then performing lewis acid catalysis, and stirring at a certain temperature for reaction for 2 to 10 hours to prepare a heptaose fragment 13; selectively eliminating $R_9$ to obtain a heptaose building block 14 with a free hydroxyl group at the C-4 site, taking 3 mol of the carbohydrate building block 1 as a glycosyl donor, taking 1 mol of the heptaose building block 14 as a glycosyl receptor, dissolving the glycosyl donor and the glycosyl receptor in dry methylene dichloride, adding a 4 Å molecular sieve, then performing lewis acid catalysis, and stirring at a certain temperature for reaction for 2 to 10 hours to prepare an octaose fragment 15;

(6) taking 1.5 mol of the disaccharide building block 6 as a glycosyl donor, taking 1 mol of the carbohydrate building block 14 as a glycosyl receptor, dissolving the glycosyl donor and the glycosyl receptor in methylene dichloride, then performing lewis acid catalysis, and stirring at a certain temperature for reaction for 2 to 10 hours to prepare a nonose fragment 16; selectively eliminating $R_9$ to obtain a nonose building block 17 with a free hydroxyl group at the C-4 site, taking 3 mol of the carbohydrate building block 1 as a glycosyl donor, taking 1 mol of the nonose building block 17 as a glycosyl receptor, dissolving the glycosyl donor and the glycosyl receptor in dry methylene dichloride, adding a 4 Å molecular sieve, then performing lewis acid catalysis, and stirring at a certain temperature for reaction for 2 to 10 hours to prepare a target decose fragment 18; and (7) by using similar methods as described above, larger polysaccharides such as a dodecylose, a tetradecaose, a hexadecylose, an octadecanose and the like can also be synthesized with the disaccharide building block 6 as a repeat unit.

Step VII, deprotection of autism-associated gram-positive bacteria (*Clostridium bolteae*) surface capsular oligosaccharide fragments such as the disaccharide, the tetrasaccharide, the hexaose, the octaose and the decose.

Formula VIII 3d, n = 0
9d, n = 1
12d, n = 2
15d, n = 3
18d, n = 4

R is —$(CH_2)_5$—$NH_2$ and is used for protecting the decose to eliminate acyl under alkaline conditions, after purification through a silicagel column, Pd/C and $H_2$ are used for elimination reaction for 3 days to eliminate aromatic groups, after deprotection of all the aromatic groups, a reversed-phase $C_{18}$ column is used for purification, and finally a target oligosaccharide fragment is obtained as in formula VIII.

The objective of the present disclosure is to, by using cheap and easy-to-obtain raw materials, provide a simple-step, time-saving, labor-saving and low-cost synthesizing method for autism-associated gram-positive bacteria (*Clostridium bolteae*) surface capsular oligosaccharide fragments which are possibly used as medicine.

The objective of the present disclosure is to apply derivatives of the gram-positive bacteria cell wall capsular polysaccharide to development or preparation of a kit for clinical diagnosis of autism.

The objective of the present disclosure is to apply the derivatives of the gram-positive bacteria cell wall capsular polysaccharide to development or preparation of medicine for controlling the number of the *C. bolteae* floras in intestinal canals of the children with the autism.

Figure 1:
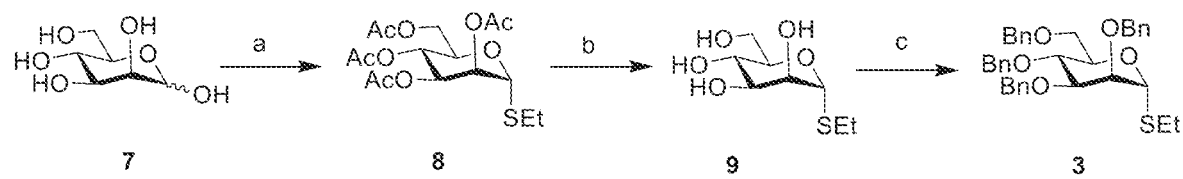
FIG. 1 is synthesis of a carbohydrate building block 3 of Example 1. Reaction conditions: (a): (1) NaOAc, $Ac_2O$, 90° C., 2 h; (2) $BF_3.Et_2O$, TMSOTf, EtSH (86%, α: β=5:1), DCM, 0° C. to r.t., 48 h; (b): MeOH, NaOMe, r.t., 48 h; (c): NaH, BnBr (85% over two steps), DMF, 0° C. to r.t., 7 h.
Figure 2:
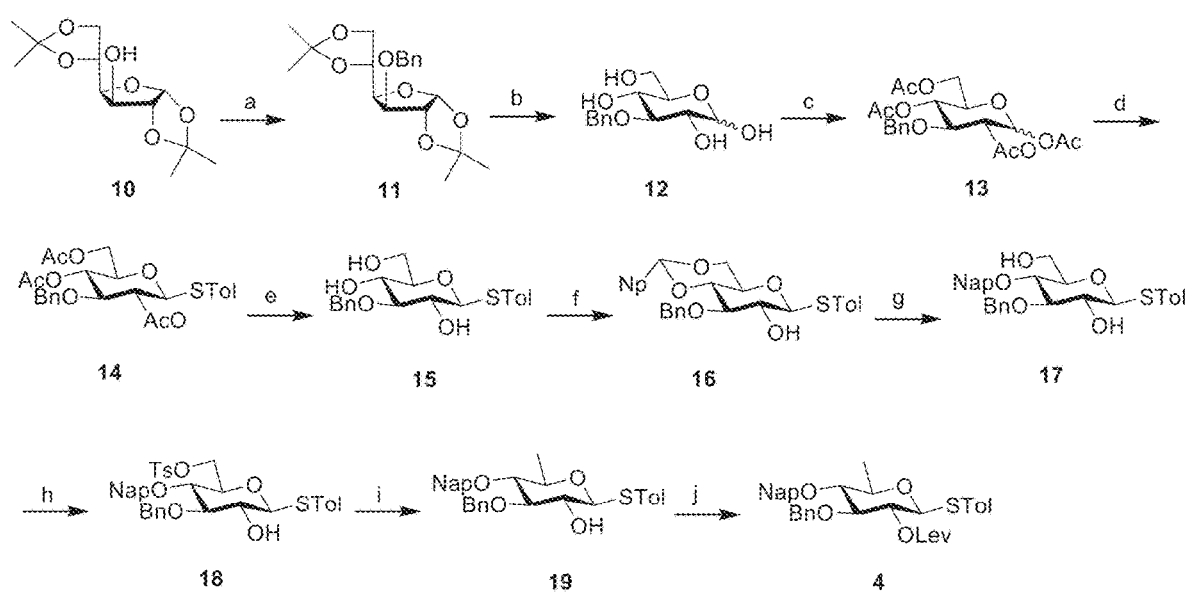
FIG. 2 is synthesis of a carbohydrate building block 4 of Example 2. Reaction conditions: (a) NaH, BnBr, DMF (99%), 0° C. to r.t., 7 h; (b): H+ resin, $CH_3COCH_3$, $H_2O$, 60° C., 48 h; (c): Py, $Ac_2O$, (85%, over two steps), 0° C. to r.t., 10 h; (d) TolSH, DCM, $BF_3.Et_2O$ (59%), 0° C. to r.t., 31 h; (e) NaOMe, MeOH, r.t., 15 h; (f) $NPCH[OCH_2CH(CH_3)_2]_2$, $CH_3CN$, TsOH (87%, over two steps), r.t., 4 h; (g) $Cu(OTf)_2$, $BH_3$.THF, $BF_3.Et_2O$ (95%), 0° C., 6 h; (h) TsCl, Py. (86%), r.t., 12 h; (i) $LiAlH_4$, THF (55%), r.t., 7 h; (j) DCC, LevOH, DMAP, DCM, (98%), r.t., 3 h.

FIG. 3 is synthesis of a carbohydrate building block 5 of Example 3. Reaction conditions: (a) $PhCH(OMe)_2$, p-TsOH, 60° C., 36 h (59%); (b) $CH_3C(OEt)_3$, p-TsOH, r.t., 3 h; (c) 80% AcOH, r.t., 1 h (83%, over two steps).

FIG. 4 is synthesis of a carbohydrate building block 6 of Example 4. Reaction conditions: (a) $HO(CH_2)_5N(Bn)Cbz$, NIS, TMSOTf, DCM 0° C., 5 h (96%, β only); (b) $H_2NNH_2$/HOAc, DCM/MeOH=20:1, r.t., 3 h (95%); (c) $(COCl)_2$, DMSO, $Et_3N$, DCM, −78° C. to r.t., 20 h (91%); (d) $NaBH_4$, EtOH, 0° C., 7 h (88%); (e) $Ac_2O$, Py, r.t., 12 h (95%); (f) DDQ, $H_2O$, DCM, r.t., 10 h (86%).

FIG. 5 is synthesis of a disaccharide building block 30 of Example 5. Reaction conditions: (a) (1) NBS, THF/$H_2O$, 7 h; (2) $Cl_3CCN$, DBU, 3 h (78%, over two steps); (b) TMSOTf, DCM, −40° C., 4 h (72%, β only); (c) $H_2NNH_2$/HOAc, 5 h (88%); (b) (1) $(COCl)_2$, DMSO, $Et_3N$, DCM, −78° C., 3 h; (2) $NaBH_4$, EtOH, 0° C., 5 h; (3) Py., $AC_2O$, 12 h (88%).

FIG. 6 is synthesis of an oligosaccharide fragment of Example 6. Reaction conditions: (a) NIS, TMSOTf, DCM, $Et_2O$, 0° C., 8 h (53-80%); (b) (1) MeONa, THF/MeOH=1:1, r.t., 12 h; (2) 80% AcOH, 70° C., 8 h; (3) $H_2$, Pd/C, DCM, t-Butanol, $H_2$, r.t., 48 h (72% over three steps); (c) NIS, TMSOTf, DCM, 0° C., 8 h (50-72%); (d) DDQ, $H_2$, DCM, r.t., 5 h (50-70%).

DETAILED DESCRIPTION

General Methods of Experiments

A drying solvent used in the experiments is dried and purified by utilizing an organic solvent purification system produced by Germany Braun Company.

$^1$H NMR, $^{13}$C NMR, 1H-1H COSY and $^1$H-$^{13}$C HSQC are assayed by Bruker AVANCE III 400 type and AVANCE 700 MHz type nuclear magnetic resonance spectrometers, wherein TMS is an internal standard, and assayed at 25° C., different peak types are represented by singlet (s), doublet (d), triplet (t), quartet (dd), multiplet (m) and the like, the unit of chemical shift (δ) is recorded as ppm, and the unit of coupling constant (J) is recorded as Hz.

High-resolution mass spectrum is assayed by MALDI SYNAPT MS type mass spectrum in a positive ion mode, and mass spectrum is assayed by Thermo Scientific TSQ Quantum Ultra mass spectrum in a positive and negative ion full scan mode. An infrared spectrogram is assayed by NICOLET IS5 infrared spectrometers and KBr pellet-pressing methods. Column chromatography and thin layer chromatography (TLC) are 200 to 300-mesh column chromatography silica gel and thin layer chromatography silica gel GF254 silica gel plates produced by Shandong Qingdao Haiyang Chemical Plant, and a color development method for experimental assay adopts 5% (v/v) sulfuric acid-ethanol solutions and ultraviolet light for color development.

Example 1 synthesis of a carbohydrate building block 3 is shown in FIG. 1:

Specific experimental operation and steps:

Compound 8: under protection of argon, commercial D-mannose (40 g, 222 mmol) is dissolved in acetic anhydride (228 mL), sodium acetate (24 g, 288.6 mmol) is added, and the mixture is stirred at 80° C. for two hours. After complete reaction of raw materials is monitored by TLC, extraction with methylene dichloride is conducted, washing with a saturated sodium bicarbonate solution is conducted, organic phases are collected, drying with anhydrous sodium sulfate is conducted, sodium sulfate is filtered out by using filter paper, and a solvent is removed through rotary evaporation to obtain a brown syrup which is directly used for next reaction. Fully acetylated mannose is dissolved in anhydrous methylene dichloride (1000 mL), a 4 Å molecular sieve is added, ethanethiol (25 mL) is added, the temperature is cooled to 0° C., a boron trifluoride ether solution (55 mL) is dropwise added, stirring is conducted for reaction for 30 minutes under an ice bath, the temperature is raised to the room temperature and stirring is conducted for reaction for 32 hours, and then 0.5 equivalent of trimethylsilyl trifluoromethanesulfonate (TMSOTf) is supplemented. After complete reaction of raw materials is monitored by TLC, triethylamine is added for quenching the reaction, a layer of diatomaceous earth is added into a sand core funnel, the molecular sieve is removed through filtering, a solvent is removed through rotary evaporation, extraction with methylene dichloride is conducted, washing with the saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→5:1) to obtain a white solid 8 (74.9 g, 191 mmol, 86% (total yield of the two-step reaction), α:β=5:1). $R_f$=0.57 (PE:EA=1:1). $^1$H NMR (400 MHz, $CDCl_3$) δ: 5.35 (dd, J=3.2, 1.5 Hz, 1H, 2-H), 5.32~5.35 (m, 1H, 4-H), 5.30 (d, J=1.6 Hz, 1H, 1-H), 5.26 (dd, J=9.9, 3.3 Hz, 1H, 3-H), 4.41 (ddd, J=9.4, 5.3, 2.2 Hz, 1H, 5-H), 4.33 (dd, J=12.2, 5.3 Hz, 1H, 6-H), 4.10 (dd, J=12.2, 2.3 Hz, 1H, 6'-H), 2.65 (m, 2H, —$CH_2$), 2.00, 2.06, 2.10, 2.18 (4s, 3H each, 4 OAc), 1.31 (t, J=7.4 Hz, 3H, Me); $^{13}$C NMR (101 MHz, $CDCl_3$) δ: 171.1, 170.4, 170.2, 170.2 82.7, 71.6, 69.9, 69.3, 66.7, 62.8, 25.9, 21.4, 21.2, 21.2, 21.1, 15.2; IR (KBr) v: 2980, 1744, 1374, 1251, 712 $cm^{-1}$; HRMS ESI-TOF: $[M+Na]^+$ calcd for $C_{16}H_{24}O_9SNa$ 415.1039; found 415.1052.

Compound 3: under protection of argon, the compound 8 (14 g, 35.6 mmol) is dissolved in methanol (90 mL), a catalytic amount of sodium methylate is added, and reaction is conducted for 2 hours at the room temperature. After complete reaction of raw materials is monitored by TLC, hydrogen ion exchange resin is added to adjust pH to 5 to 6, the resin is filtered out by using filter paper, and a solvent is removed through rotary evaporation to obtain a brown syrup which is directly used for next reaction. The obtained syrup is dissolved in dimethylformamide (120 mL), the temperature is cooled to 0° C., sodium hydride (11.4 g, 284.8 mmol) is added, benzyl bromide (26 mL) is dropwise added, reaction is conducted for 30 minutes under an ice bath, and the temperature is raised to the room temperature for reaction for 7 hours. After complete reaction of raw materials is monitored by TLC, ice water is added to stop the reaction, extraction with methylene dichloride is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=100:1→10:1) to obtain a white solid 3 (17.7 g, 30.3 mmol, 85% (total yield of the two-step reaction)). $R_f$=0.63 (PE:EA=7:3). $^1$H NMR (400 MHz, CDCl$_3$) δ: 7.63~7.01 (m, 20H, 4 Ph), 5.40 (d, J=1.3 Hz, 1H, 1-H), 5.03~4.45 (m, 8H, 4 PhCH$_2$), 4.13 (ddd, J=9.9, 4.8, 1.9 Hz, 1H, 5-H), 4.03 (td, J=10.1, 1.3 Hz, 1H, 3-H), 3.86~3.78 (m, 3H, 2, 6, 6'-H), 3.71 (dd, J=10.9, 1.9 Hz, 1H, 4-H), 2.70~2.47 (m, 2H, SEt-CH$_2$), 1.24 (t, J=7.4 Hz, 3H, SEt-CH$_3$); $^{13}$C NMR (101 MHz, CDCl$_3$) δ: 138.7, 138.5, 138.4, 138.3, 128.5, 128.5, 128.4, 128.4, 128.0, 128.0, 127.9, 127.8, 127.8, 127.7, 127.6, 82.0, 80.5, 76.5, 75.2, 75.2, 73.4, 72.2, 72.1, 72.1, 69.3, 25.4, 15.1.

Example 2 synthesis of a carbohydrate building block 4 is shown in FIG. 2:

Specific experimental operation and steps:

Compound 11: under protection of argon, commercial diacetone glucose 10 (50 g, 191 mmol) is dissolved in dimethylformamide (490 mL), the temperature is cooled to 0° C., sodium hydride (15.4 g, 382 mmol) is added several times, benzyl bromide (35 mL) is dropwise added, reaction is conducted for 30 minutes under an ice bath, and the temperature is raised to the room temperature for reaction for 5 hours. After complete reaction of raw materials is monitored by TLC, ice water is added to stop the reaction, extraction with methylene dichloride (3×250 mL) is conducted, organic phases are collected, drying with anhydrous sodium sulfate is conducted, sodium sulfate is filtered out by using filter paper to obtain a syrup 11 (66.2 g, 189.1 mmol, 99%). $^1$H NMR (400 MHz, CDCl$_3$) δ: 7.61~7.08 (m, 5H, Ph), 5.90 (d, J=3.7 Hz, 1H, 1-H), 4.68 (d, J=11.8 Hz, 1H, PhCH), 4.63 (d, J=11.8 Hz, 1H, PhCH), 4.58 (d, J=3.7 Hz, 1H, 2-H), 4.37 (dt, J=7.7, 6.1 Hz, 1H, 5-H), 4.15 (dd, J=7.8, 3.2 Hz, 1H, 6-H), 4.11 (dd, J=9.1, 6.7 Hz, 1H, 6'-H), 4.01 (dd, J=8.1, 2.7 Hz, 1H, 4-H), 3.99 (m, 1H, 3-H), 1.49 (s, 3H, CH$_3$), 1.43 (s, 3H, CH$_3$), 1.37 (s, 3H, CH$_3$), 1.31 (s, 3H, CH$_3$); $^{13}$C NMR (101 MHz, CDCl$_3$) δ: 137.8, 128.5, 128.0, 127.8, 111.9, 109.1, 105.4, 82.8, 81.8, 81.5, 72.7, 72.5, 67.5, 27.0, 26.9, 26.4, 25.6.

Compound 13: under protection of argon, the compound 11 (66.2 g, 189.1 mmol) is dissolved in acetone (45 mL) and deionized water (425 mL), Amberlite IR120 hydrogen ion exchange resin (85 g) is added, the obtained mixture is heated to 60° C. and subjected to reflux condensation for 2 days. After complete reaction of raw materials is monitored by TLC, the temperature is cooled to the room temperature, the resin is filtered out by using filter paper, the resin is washed with methanol, a saturated sodium bicarbonate solution is added to adjust pH of the solution to neutral, and a solvent is removed through rotary evaporation to obtain a brown syrup. The brown syrup is dissolved with toluene, dehydrated through rotary evaporation azeotropy and placed on oil pump overnight for vacuumizing, and then is directly used for next step reaction. The obtained syrup is dissolved in dry pyridine (425 mL), the temperature is cooled to 0° C., acetic anhydride (80 mL) is dropwise added, reaction is conducted for 30 minutes under an ice bath, the temperature is raised to the room temperature and stirring is conducted for reaction for 10 hours. After complete reaction of raw materials is monitored by TLC, a solvent is removed through rotary evaporation, extraction with methylene dichloride (3×200 mL) is conducted, sequential washing with 1 mmol·L$^{-1}$ hydrochloric acid and a saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=100:1→2:1) to obtain a brown syrup 13 (70.5 g, 160.7 mmol, 85% (total yield of the two-step reaction α:β=1:3)). $R_f$=0.32 (PE:EA=7:3). α 构型: $^1$H NMR (400 MHz, CDCl$_3$) δ: 7.36~7.19 (m, 5H, Ph), 6.31 (d, J=3.6 Hz, 1H, 1-H), 5.16 (t, J=9.8 Hz, 1H, 4-H), 5.05 (dd, J=10.0, 3.7 Hz, 1H, 2-H), 4.71 (d, J=11.8 Hz, 1H, Ph-CH), 4.63 (d, J=11.8 Hz, 1H, Ph-CH), 4.24~4.16 (m, 1H, 6-H), 4.09~3.92 (m, 3H, 3, 5, 6'-H), 2.16 (s, 3H, OAc), 2.07 (s, 3H, OAc), 1.99 (s, 3H, OAc), 1.97 (s, 3H, OAc); $^{13}$C NMR (101 MHz, CDCl$_3$) δ: 170.6, 170.5, 169.5, 169.2, 168.7, 137.9, 128.4, 127.7, 127.4, 89.4, 76.9, 74.8, 71.5, 70.2, 69.1, 69.1, 61.8, 20.8, 20.7, 20.6, 20.5.

Compound 14: under protection of argon, the compound 13 (70.5 g, 161 mmol) and a pre-activated 4 Å molecular sieve are mixed, anhydrous methylene dichloride (610 mL) is added, p-toluenethiol (30 g, 242 mmol) is added, the temperature is cooled to 0° C., stirring is conducted for 1 hour, boron trifluoride ether solution is (70 mL, 484.6 mmol) is dropwise added, the temperature is raised to the room temperature and stirring is conducted for reaction for 30 hours. After complete reaction of raw materials is monitored by TLC, the temperature is cooled to 0° C., triethylamine is added for quenching the reaction, the molecular sieve is filtered out by using diatomaceous earth, a solvent is removed through rotary evaporation, washing with a saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=100:1→10:1) to obtain a white solid 14 (52.6 g, 104.7 mmol, 65%). $R_f$=0.42 (PE:EA=7:3). $^1$H NMR (400 MHz, CDCl$_3$) δ: 7.45~6.91 (m, 9H, Ph), 5.03 (dt, J=15.0, 9.6 Hz, 2H, 2, 4-H), 4.64~4.51 (m, 3H, 4-H, Ph-CH$_2$), 4.16 (t, J=3.4 Hz, 2H, 6, 6'-H), 3.71 (t, J=9.2 Hz, 1H, 3-H), 3.60 (ddd, J=9.9, 5.0, 3.1 Hz, 1H, 5-H), 2.33 (d, J=1.8 Hz, 3H, STol-CH$_3$), 2.07 (s, 3H, OAc), 2.04 (s, 3H, OAc), 1.95 (s, 3H, OAc); $^{13}$C NMR (101 MHz, CDCl$_3$) δ: 170.8, 170.7, 169.4, 169.3, 138.5, 138.5, 137.9, 137.8, 133.4, 133.4, 129.7, 128.7, 128.7, 128.6, 128.5, 128.0, 127.9, 86.5, 81.7, 77.6, 77.3, 76.9, 76.2, 74.4, 74.3, 71.5, 71.5, 69.8, 69.8, 62.7, 21.3, 21.1, 20.9, 20.9, 20.8.

Compound 16: under protection of argon, the compound 14 (40.7 g, 81 mmol) is dissolved in methanol (300 mL), a catalytic amount of sodium methylate is added, and reaction is conducted at the room temperature for 15 hours. After an insoluble substance is completely dissolved and becomes a clear solution, and complete reaction of raw materials is monitored by TLC, cation exchange resin is added to adjust pH to 5 to 6, the resin is filtered out by using filter paper, a solvent is removed through rotary evaporation to obtain a compound 15, which is directly applied to next step reaction without purification. The compound 15 is dissolved in dry acetonitrile (450 mL), 2-(isobutyric methoxy)-methylnaphthalene (46 g, 162 mmol) and p-toluenesulfonic acid (769 mg, 4 mmol) are added, stirring is conducted at the room temperature, the solution slowly becomes clear, and quickly condenses into white solid, and stirring is conducted at the room temperature for 4 hours. After complete reaction of raw materials is monitored by TLC, washing with a saturated sodium bicarbonate solution is conducted, extraction with methylene dichloride is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=100:1→10:1) to obtain a white solid 16 (37.3 g, 70.5 mmol, 87% (total yield of two-step reaction)). $R_f$=0.39 (PE:EA=4:1). $^1$H NMR (400 MHz, CDCl$_3$) δ: 8.17~6.86 (m, 16H, Ph), 5.72 (s, 1H, Np—CH), 4.97 (d, J=11.6 Hz, 1H, Ph-CH), 4.83 (d, J=11.6 Hz, 1H, Ph-CH), 4.59 (d, J=9.7 Hz, 1H, 1-H), 4.44 (dd, J=10.5, 5.0 Hz, 1H, 6-H), 3.85 (t, J=10.3 Hz, 1H, 6'-H), 3.71 (dd, J=7.1, 4.5 Hz, 2H, 3, 4-H), 3.53 (ddt, J=14.9, 5.5, 3.7 Hz, 2H, 2, 5-H), 2.59 (d, J=2.2 Hz, 1H, 2-OH), 2.36 (s, 3H, STol-CH$_3$); $^{13}$C NMR (101 MHz, CDCl$_3$) δ: 138.9, 138.4, 134.7, 1340, 133.8, 133.0, 130.0, 128.6, 128.5, 128.2, 128.2, 128.0, 127.8, 127.4, 126.6, 126.3, 125.6, 123.8, 101.6, 88.8, 81.8, 81.4, 77.4, 75.0, 72.4, 70.9, 68.9, 21.3.

Compound 17: under protection of argon, the compound 16 (20.3 g, 38.4 mmol) is dissolved in a borane-tetrahydrofuran solution (425 mL), the temperature is cooled to 0° C., stirring is conducted for 30 minutes, copper trifluoromethanesulfonate (4.1 g, 11.5 mmol) and boron trifluoride ether (0.5 mL) are added, and stirring is conducted for reaction for 6 hours under an ice bath. After complete reaction of raw materials is monitored by TLC, ice water is dropwise added, excess borane is removed, washing with a saturated sodium bicarbonate solution is conducted, extraction with methylene DIchloride is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=50:1→5:1) to obtain a white solid 17 (18.8 g, 36.5 mmol, 95%). $R_f$=0.27 (PE:EA=7:3). $^1$H NMR (400 MHz, CDCl$_3$) δ: 8.13~7.05 (m, 16H, Ph), 5.17~4.66 (m, 4H, Ph-CH$_2$), 4.51 (d, J=9.7 Hz, 1H, 1-H), 3.93 (ddd, J=12.0, 5.9, 2.5 Hz, 1H, 6-H), 3.74 (ddd, J=12.1, 7.6, 4.7 Hz, 1H, 6'-H), 3.65 (t, J=8.7 Hz, 1H, 3-H), 3.58 (t, J=9.2 Hz, 1H, 4-H), 3.47 (ddd, J=10.1, 8.1, 2.3 Hz, 2H, 2, 5-H), 2.50 (d, J=2.2 Hz, 1H, 2-OH), 2.35 (s, 3H, STol-CH$_3$), 1.99 (dd, J=7.5, 6.0 Hz, 1H, 6-OH); $^{13}$C NMR (101 MHz, CDCl$_3$) δ: 138.8, 138.6, 135.5, 133.7, 133.4, 133.2, 130.0, 128.6, 128.4, 128.1, 128.1, 127.9, 127.8, 127.7, 126.9, 126.3, 126.1, 126.0, 88.5, 85.9, 79.8, 77.5, 75.5, 75.3, 73.0, 62.4, 21.3.

Compound 18: under protection of argon, the compound 17 (3.9 g, 7.7 mmol) is dissolved in dry pyridine (40 mL), tosyl chloride (2.9 g, 15.4 mmol) is added several times, and stirring is conducted for reaction for 12 hours at the room temperature. After complete reaction of raw materials is monitored by TLC, ice water is dropwise added to stop the reaction, extraction with methylene dichloride is conducted, sequential washing with 1 mmol-L-hydrochloric acid and a saturated sodium bicarbonate solution is conducted, organic phases are collected, drying with anhydrous sodium sulfate is conducted, the organic phases are collected, sodium sulfate is filtered out by using filter paper, a solvent is removed through rotary evaporation, and a crude product is purified by silica gel column chromatography (PE:EA=50:1→8:1) to obtain a syrup 18 (4.5 g, 6.6 mmol, 85%). $R_f$=0.33 (PE:EA=7:3). 1H NMR (400 MHz, CDCl3) δ: 8.10~6.84 (m, 20H, Ph), 5.05~4.55 (m, 4H, Ph-CH2), 4.35 (d, J=9.6 Hz, 1H, 1-H), 4.29 (dd, J=10.6, 1.9 Hz, 1H, 6-H), 4.14 (dd, J=10.6, 4.6 Hz, 1H, 6'-H), 3.58 (t, J=8.6 Hz, 1H, 3-H), 3.53 (ddd, J=9.8, 4.6, 1.9 Hz, 1H, 5-H), 3.46 (dd, J=9.8, 8.5 Hz, 1H, 4-H), 3.37 (dd, J=9.7, 8.6 Hz, 1H, 2'-H), 2.33 (d, J=2.2 Hz, 6H, STol-CH3, Ts-CH3); 13C NMR (101 MHz, CDCl3) δ: 145.0, 138.8, 138.4, 135.1, 133.9, 133.4, 133.2, 132.9, 130.0, 129.9, 128.7, 128.4, 128.1, 128.1, 128.0, 127.8, 127.1, 127.0, 126.3, 126.2, 126.0, 88.1, 85.7, 77.4, 76.9, 76.5, 75.5, 75.3, 72.4, 68.6, 21.7, 21.3.

Compound 19: under protection of argon, the compound 18 (2.9 g, 4.5 mmol) is dissolved in dry tetrahydrofuran (33 mL), lithium aluminium hydride (837 mg, 22.5 mmol) is added several times, and stirring is conducted for reaction for 7 hours at the room temperature. After complete reaction of raw materials is monitored by TLC, ice water is dropwise added to stop the reaction, excess lithium aluminium hydride is removed, extraction with methylene dichloride is conducted, sequential washing with 1 mmol·L$^{-1}$ hydrochloric acid and a saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=50:1→10:1) to obtain a white solid 19 (1.3 g, 2.5 mmol, 55%). $R_f$=0.53 (PE:EA=7:3). $^1$H NMR (400 MHz, CDCl$_3$) δ: 8.04~6.83 (m, 16H, Ph), 5.10~4.69 (m, 4H, Ph-CH$_2$), 4.43 (d, J=9.7H·z, 1H, 1-H), 3.59 (t, J=8.8 Hz, 1H, 3-H), 3.51~3.40 (m, 2H, 2, 5-H), 3.20 (t, J=9.1 Hz, 1H, 4-H), 2.33 (s, 3H, STol-CH$_3$), 1.36 (d, J=6.1 Hz, 3H, 6-H); $^{13}$C NMR (101 MHz, CDCl$_3$) δ: 138.7, 138.5, 135.7, 133.6, 133.4, 133.1, 129.9, 128.6, 128.3, 128.1, 128.0, 128.0, 127.9, 127.8, 126.8, 126.2, 126.1, 88.4, 85.9, 83.0, 76.0, 75.5, 74.4, 73.1, 21.3, 18.5.

Compound 4: under protection of argon, the compound 19 (1.6 g, 3.3 mmol) is dissolved in dry methylene dichloride (17 mL), dicyclohexylcarbodiimide (867 mg, 4.2 mmol) acetylpropionic acid (488 mg, 4.2 mmol) and dimethylaminopyridine (475 mg, 3.9 mmol) are added, and stirring is conducted for reaction for 3 hours at the room temperature. After complete reaction of raw materials is monitored by TLC, insoluble while solid is filtered out, extraction with methylene dichloride is conducted, washing with a saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=50:1→10:1) to obtain a white solid 4 (1.9 g, 3.2 mmol, 96%). $R_f$=0.53 (PE:EA=7:3). $^1$H NMR (400 MHz, Chloroform-d) δ:7.77~6.79 (m, 16H, Ph), 5.00~4.94 (m, 2H, 2-H, Ph-CH$_2$), 4.83~4.68 (m, 3H, Ph-CH$_2$), 4.54 (d, J=10.1 Hz, 1H, 1-H), 3.68 (t, J=9.0 Hz, 1H, 3-H), 3.45 (dq, J=9.4, 6.1 Hz, 1H, 5-H), 3.29 (t, J=9.2 Hz, 1H, 4-H), 2.73 (td, J=6.7, 6.3, 3.0 Hz, 2H, Lev-CH$_2$), 2.54 (qt, J=17.2, 6.7 Hz, 2H, Lev-CH$_2$), 2.32 (s, 3H, STol-CH$_3$), 2.16 (s, 3H, Lev-CH$_3$), 1.35 (d, J=6.1 Hz, 3H, 6-H); $^{13}$C NMR (101 MHz, CDCl$_3$) δ: 206.2, 171.5, 138.3, 138.2, 135.5, 133.3, 133.1, 129.7, 129.2, 128.5, 128.3, 128.0, 128.0, 127.8, 127.8, 126.9, 126.2, 126.1, 126.1, 86.4, 84.3, 83.2, 75.9, 75.5, 75.3, 72.7, 38.0, 30.0, 28.3, 21.3, 18.3.

Figure 3:
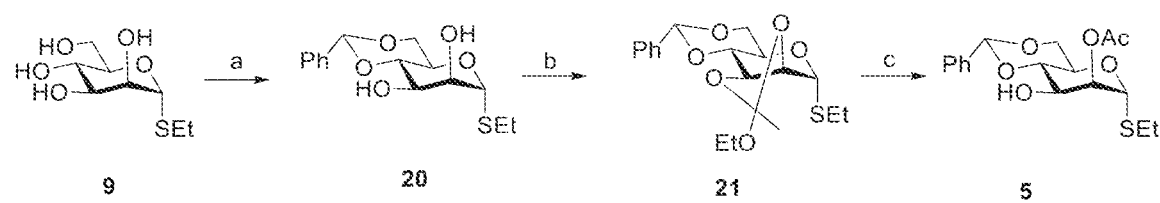

Example 3 synthesis of a carbohydrate building block 5 is shown in FIG. 3:

Compound 20: under protection of argon, the compound 8 (11.3 g, 28.7 mmol) is dissolved in methanol (250 mL), a catalytic amount of sodium methylate is added, and reaction is conducted for 12 hours at the room temperature. After complete reaction of raw materials is monitored by TLC, cation exchange resin is added to adjust pH to 5 to 6, the resin is filtered out by using filter paper, and a solvent is removed through rotary evaporation to obtain a brown syrup which is directly used for next reaction. The obtained syrup is dissolved in dimethylformamide (90 mL), stirring is conducted at the room temperature, p-toluenesulfonic acid (735 mg, 3.9 mmol) and benzaldehyde dimethyl acetal (5 mL, 32.8 mmol) are added, and the temperature is raised to 60° C. for reaction for 7 hours. After complete reaction of raw materials is monitored by TLC, triethylamine (5 mL) is added to stop the reaction, extraction with methylene dichloride (3×150 mL) is conducted, washing with a saturated sodium bicarbonate solution (3×150 mL) is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=10:1→1:1) to obtain a white solid 20 (5.3 g, 16.9 mmol, 59% (total yield of the two-step reaction)). $R_f$=0.21 (PE:EA=1:1). $^1$H NMR (400 MHz, CD$_3$OD) δ:7.35~7.54 (m, 5H, Ph), 5.32 (s, 1H, Ph-CH), 5.32 (d, J=1.3 Hz, 1H, 1-H), 4.15 (m, 1H), 4.18 (m, 1H), 4.02 (dd, J=3.4, 1.3 Hz, 1H, 2-H), 3.90 (m, 1H), 3.99 (m, 1H), 3.87 (m, 1H), 2.68 (m, 2H, SEt-CH$_2$), 1.33 (s, 3H, SEt-CH$_3$); $^{13}$C NMR (101 MHz, CD$_3$OD) δ:139.3, 129.9, 129.0 127.5, 103.4, 87.3, 80.4, 74.3, 70.0, 69.6, 65.7, 26.0, 15.4; IR (KBr) v: 3434, 2937, 1750, 1224, 1045 cm$^{-1}$; HRMS ESI-TOF: [M+Na]$^+$ calcd for C$_{15}$H$_{20}$O$_5$SNa 335.0929; found 335.1031.

Compound 5: under protection of argon, the compound 20 (1.03 g, 3.3 mmol) is dissolved in anhydrous methylene dichloride (22 mL), triethyl orthoacetate (6 mL, 32.9 mmol) and p-toluenesulfonic acid (113 mg, 0.6 mmol) are added, and reaction is conducted for 20 minutes at the room temperature. After complete reaction of raw materials is monitored by TLC, extraction with methylene dichloride (3×50 mL) is conducted, washing with a saturated sodium bicarbonate solution (3×50 mL) is conducted, drying with anhydrous sodium sulfate is conducted, sodium sulfate is filtered out by using filter paper, a solvent is removed through rotary evaporation, an obtained crude product is directly used for next step reaction without purification, 80% acetum (11 mL) is added, and reaction is conducted for 30 minutes at the room temperature. After complete reaction of raw materials is monitored by TLC, extraction with methylene dichloride (3×50 mL) is conducted, washing with a saturated sodium bicarbonate solution (3×50 mL) is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=10:1→4:1) to obtain a syrup 5 (971 mg, 2.7 mmol, 83% (total yield of the two-step reaction)). $R_f$=0.61 (PE:EA=1:1). $^1$H NMR (400 MHz, CDCl$_3$) δ: 7.56~7.34 (m, 5H, Ph), 5.60 (s, 1H, Ph-CH), 5.30 (dd, J=3.7, 1.3 Hz, 1H, 2-H), 5.27 (d, J=1.3 Hz, 1H, 1-H), 4.29~4.23 (m, 2H, 5, 6-H), 4.20~4.16 (m, 1H, 3-H), 3.94 (t, J=9.5 Hz, 1H, 4-H), 3.89~3.81 (m, 1H, 6'-H), 2.65 (qq, J=12.9, 7.4 Hz, 2H, SEt-CH$_2$), 2.43 (d, J=4.0 Hz, 1H, 3-OH), 2.18 (s, 3H, OAc), 1.30 (t, J=7.4 Hz, 3H, SEt-CH$_3$); $^{13}$C NMR (101 MHz, CDCl$_3$) δ: 170.6, 170.6, 137.2, 129.4, 129.4, 128.5, 128.5, 126.4, 102.4, 83.5, 83.4, 79.4, 77.4, 74.0, 74.0, 68.7, 67.9, 64.2, 64.2, 25.8, 21.2, 21.2, 15.0; IR (KBr) v: 3451, 1739, 1229, 902 cm$^{-1}$; HRMS ESI-TOF: [M+Na]$^+$ calcd for C$_{17}$H$_{22}$O$_6$SNa 337.1035; found 337.1039.

Figure 4:
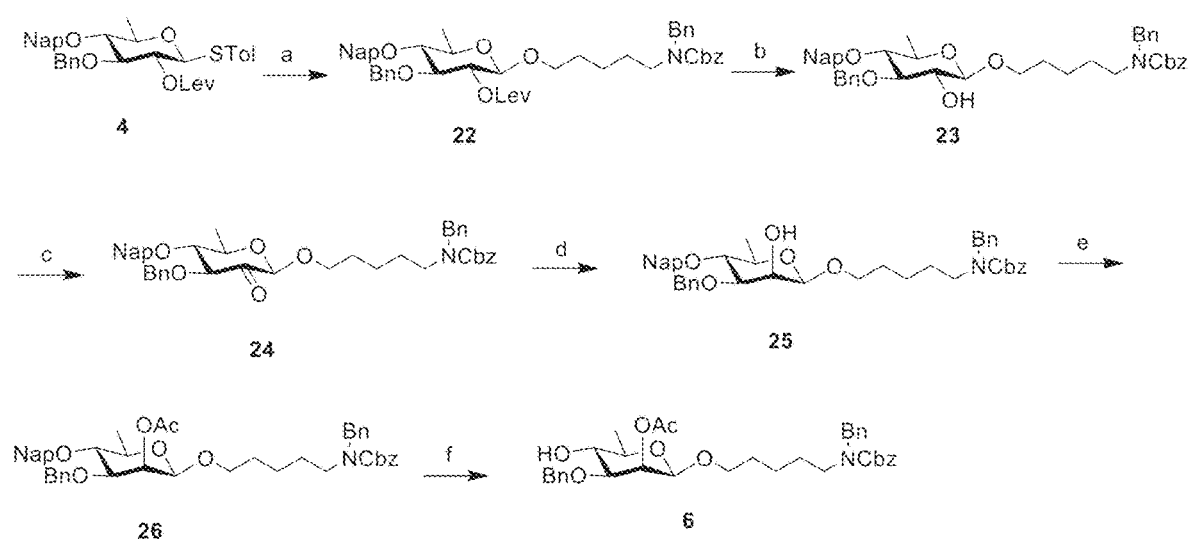

Example 4 synthesis of a carbohydrate building block 6 is shown in FIG. 4:

Specific experimental operation and steps:

Compound 22: under protection of argon, the compound 4 (557 mg, 0.93 mmol) and N-(benzyl)-carbobenzoxy-5-amino-1-amyl alcohol (700 mg, 2.14 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (2 mL) is added, iodosuccinimide (252 mg, 1.2 mmol) is added, the temperature is cooled to 0° C., stirring is conducted for 30 minutes, trimethylsilyl trifluoromethanesulfonate (20 μL) is dropwise added, and stirring is conducted for reaction for 5 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, extraction with methylene dichloride is conducted, washing with the saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→4:1) to obtain a syrup 22 (716 g, 0.89 mmol, 96%). $R_f$=0.28 (PE:EA=7:3). $^1$H NMR (400 MHz, CDCl$_3$) δ: 8.18~6.82 (m, 22H, Ph), 5.17 (d, J=3.6 Hz, 2H, Ph-CH$_2$), 4.99 (d, J=3.6 Hz, 1H, Ph-CH$_2$), 4.97 (d, J=1.9 Hz, 1H, 2-H), 4.86~4.67 (m, 3H, Ph-CH$_2$), 4.49 (d, J=6.1 Hz, 2H, Ph-CH$_2$), 4.31 (d, J=7.4 Hz, 1H, 1-H), 3.78 (d, J=12.3 Hz, 1H, linker-OCH$_2$), 3.66 (t, J=9.2 Hz, 1H, 3-H), 3.47~3.35 (m, 2H, 5-H), 3.31 (t, J=9.1 Hz, 1H, 4-H), 3.27~3.12 (m, 2H, linker-NCH$_2$), 2.77~2.57 (m, 2H, Lev-CH$_2$), 2.47 (q, J=7.0 Hz, 2H, Lev-CH$_2$), 2.11 (s, 3H, Lev-CH$_3$), 1.60~1.46 (m, 4H, linker-CH$_2$), 1.32 (d, J=6.1 Hz, 3H, 6-H), 1.28~1.10 (m, 2H, linker-CH$_2$); $^{13}$C NMR (101 MHz, CDCl$_3$) δ: 206.2, 171.5, 156.8, 156.3, 138.4, 138.1, 136.9, 135.5, 133.4, 133.1, 128.6, 128.6, 128.5, 128.4, 128.3, 128.3, 128.0, 128.0, 127.9, 127.9, 127.8, 127.4, 127.3, 126.9, 126.2, 126.1, 100.8, 83.5, 82.9, 77.4, 75.5, 75.1, 74.0, 71.5, 69.5, 67.2, 50.6, 50.3, 47.2, 46.3, 37.9, 30.0, 29.3, 28.1, 27.5, 23.2, 18.0.

Compound 23: under protection of argon, the compound 22 (716 mg, 0.89 mmol) is dissolved in methylene dichloride (4.8 mL), methanol (0.3 mL) is added, hydrazine acetate (140 mg, 1.5 mmol) is added, and stirring is conducted for reaction for 4 hours at the room temperature. After complete reaction of raw materials is monitored by TLC, a solvent is removed through rotary evaporation, and a crude product is purified by silica gel column chromatography (PE:EA=20:1→4:1) to obtain a syrup 23 (595 mg, 0.85 mmol, 95%). $R_f$=0.37 (PE:EA=7:3). $^1$H NMR (400 MHz, CDCl$_3$) δ: 8.67~7.04 (m, 22H, Ph), 5.20 (d, J=9.3 Hz, 2H, Ph-CH$_2$), 5.10~4.80 (m, 2H, Ph-CH$_2$), 4.86 (dd, J=25.0, 11.2 Hz, 2H, Ph-CH$_2$), 4.51 (d, J=8.9 Hz, 2H, Ph-CH$_2$), 4.23 (d, J=8.4 Hz, 1H, 1-H), 4.00~3.75 (m, 1H, linker-OCH$_2$), 3.66~3.50 (m, 2H, 2, 3-H), 3.50~3.35 (m, 2H, 4-H, linker-OCH$_2$), 3.35~3.15 (m, 3H, 5-H, linker-NCH$_2$), 1.67~1.18 (m, 9H, 6-H, linker-CH$_2$); $^{13}$C NMR (101 MHz, CDCl$_3$) δ: 156.9, 156.4, 138.9, 138.0, 136.9, 135.8, 133.4, 133.1, 128.6, 128.6, 128.3, 128.1, 128.0, 128.0, 127.9, 127.8, 127.4, 126.8, 126.2, 126.1, 126.0, 102.8, 84.5, 83.3, 77.4, 75.5, 75.2, 71.6, 70.0, 69.8, 67.3, 50.6, 50.4, 47.2, 46.2, 34.1, 29.3, 28.0, 27.5, 25.1, 23.4, 18.2, 0.1.

Compound 24: under protection of argon, oxalyl chloride (4.3 mL, 50 mmol) is dissolved in anhydrous methylene dichloride (15 mL), and stirring is conducted at −78° C. Under protection of argon, dimethylsulfoxide (8.6 mL, 100 mmol) is dissolved in anhydrous methylene dichloride (15 mL) through dropwise adding, and stirring is conducted for reaction for 1 hour at −78° C. after dropwise adding is completed. A carbohydrate building block 23 (3.5 g, 5 mmol) is dissolved in anhydrous methylene dichloride (14 mL), the mixture is dropwise added into a reaction system under protection of argon, and stirring is conducted for reaction for 0.5 hour at minus 78° C. after dropwise adding is completed. Then, under protection of argon, triethylamine (14 mL, 100 mmol) is dropwise added, a white solid slowly appears, the temperature is slowly raised to the room temperature from −78° C. after dropwise adding is completed, and stirring is conducted for reaction for 12 hours. After complete reaction of raw materials is monitored by TLC, washing with a 10% (w/w) sodium thiosulfate solution is conducted, organic phases are collected, dewatering and drying with anhydrous sodium sulfate are conducted, a solvent is removed through filtration and spin-drying, and a crude product is purified by silica gel column chromatography (PE:EA=20:1→3:1) to obtain a product 24 (3.2, 4.6 mmol, 91%). $R_f$=0.37 (PE:EA=7:3). $^1$H NMR (400 MHz, CDCl$_3$) δ: 7.85~7.07 (m, 22H, Ph), 5.20~5.07 (m, Ph-CH$_2$), 5.05~4.97 (m, 2H, Ph-CH$_2$), 4.76 (d, J=11.2 Hz, 2H, Ph-CH$_2$), 4.57 (m, 2H, Ph-CH$_2$), 4.17 (d, J=9.0 Hz, 1H, 1-H), 3.87~3.65 (m, 2H, linker-OCH$_2$, 5-H), 3.56~3.45 (m, 2H, 3, 4-H), 3.45~3.35 (m, 1H, linker-OCH$_2$), 3.28~3.10 (m, 2H, linker-NCH$_2$), 1.65~1.15 (m, 9H, 6-H, linker-CH$_2$). $^{13}$C NMR (101 MHz, CDCl$_3$) δ: 200.2, 197.5, 156.8, 156.3, 138.0, 137.5, 137.2, 136.9, 135.3, 135.1, 133.3, 133.3, 133.2, 128.6, 128.6, 128.6, 128.6, 128.4, 128.3, 128.3, 128.2, 128.2, 128.1, 128.0, 128.0, 127.9, 127.9, 127.8, 127.4, 127.3, 127.1, 126.9, 126.3, 126.3, 126.2, 126.2, 126.1, 125.9, 99.3, 85.9, 85.4, 82.0, 77.4, 76.8, 75.4, 73.6, 72.7, 72.5, 72.3, 72.1, 69.5, 67.3, 50.6, 50.3, 47.2, 46.2, 29.3, 28.0, 27.5, 23.3, 19.1, 18.2.

Compound 25: the compound 24 and methylbenzene are subjected to azeotropic dewatering three times, under protection of argon, the compound 24 is dissolved in anhydrous ethanol (40 mL), the temperature is cooled to 0° C. or below and stirring is conducted, sodium borohydride (253 mg, 6.7 mmol) is added, and stirring is conducted for reaction for 30 h at 0° C. After complete reaction of raw materials is monitored by TLC, an insoluble substance is filtered out, washing with a saturated sodium chloride solution is conducted, organic phases are collected, dewatering and drying with anhydrous sodium sulfate are conducted, a solvent is removed through filtration and spin-drying, and a crude product is purified by silica gel column chromatography (PE:EA=10:1→4:1) obtain a syrup 25 (2.8 g, 4.0 mmol, 88%). $R_f$=0.61 (PE:EA=1:1). $^1$H NMR (400 MHz, CDCl$_3$) δ: 7.85~7.12 (m, 22H, Ph), 5.17 (m, 2H, Ph-CH$_2$), 5.09 (d, J=11.1 Hz, 1H, Ph-CH$_2$), 4.82~4.65 (m, 3H, Ph-CH$_2$), 4.49 (d, J=5.8 Hz, 2H, Ph-CH$_2$), 4.34 (d, J=11.2 Hz, 1H, 1-H), 4.09 (s, 1H, 2-H), 3.83 (d, J=15 Hz, 1H, linker-OCH$_2$), 3.63~3.53 (m, 2H, 3-H, 4-H), 3.43 (d, J=15 Hz, 1H, linker-OCH$_2$), 3.34 (m, 1H, 5-H), 3.30~3.15 (m, 2H, linker-NCH$_2$), 2.42 (d, J=26.4 Hz, 1H, 2-OH), 1.65~1.65 (m, 4H, linker-CH$_2$), 1.35 (d, J=6.2 Hz, 3H, 6-H), 1.32~1.29 (m, 2H, linker-CH$_2$); $^{13}$C NMR (101 MHz, CDCl$_3$) δ: 156.8, 156.3, 152.6, 138.0, 138.0, 137.0, 136.0, 133.4, 133.1, 128.6, 128.6, 128.5, 128.4, 128.2, 128.0, 128.0, 127.9, 127.8, 127.8, 127.5, 127.4, 126.9, 126.8, 126.3, 126.2, 126.0, 125.9, 102.3, 101.0, 99.7, 99.3, 81.6, 81.3, 79.8, 77.4, 75.6, 71.6, 71.4, 69.6, 69.4, 69.2, 68.9, 68.6, 67.3, 66.7, 50.6, 50.4, 47.2, 46.3, 29.5, 29.3, 28.0, 27.6, 23.4, 22.4, 18.1.

Compound 26: under protection of argon, the compound 25 (2.8 g, 4 mmol) is dissolved in dry pyridine (20 mL), the temperature is cooled to 0° C., hydrazine acetate (1 mL) is dropwise added, dimethylformamide (DMAP) (96.8 mg, 0.8 mmol) is added, reaction is conducted for 30 minutes under an ice bath, the temperature is raised to the room temperature and stirring is conducted for reaction for 10 hours. After complete reaction of raw materials is monitored by TLC, extraction with methylene dichloride (3×200 mL) is conducted, sequential washing with 1 mmol·L$^{-1}$ hydrochloric acid and a saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→3:1) to obtain a brown syrup 26 (2.8 g, 3.8 mmol, 95%). $R_f$=0.52 (PE:EA=7:3). $^1$H NMR (400 MHz, CDCl$_3$) δ: 7.85~7.05 (m, 22H, Ph), 5.60 (s, 1H, 2-H), 5.17 (d, J=11.8 Hz, 2H, Ph-CH$_2$), 5.07 (d, J=11.0 Hz, 1H, Ph-CH$_2$), 4.77 (d, J=11.1 Hz, 2H, Ph-CH$_2$), 4.52 (s, 1H, 1-H), 4.51~4.40 (m, 3H, Ph-CH$_2$), 4.20~4.04 (m, 1H, linker-OCH$_2$), 3.79 (ddd, J=6.9, 5.7, 3.2 Hz, 1H, linker-OCH$_2$), 3.64 (dd, J=9.1, 3.3 Hz, 1H, 3-H), 3.47 (t, J=9.2 Hz, 1H, 4-H), 3.39 (dd, J=9.4, 5.9 Hz, 1H, 5-H), 3.30~3.08 (m, 2H, linker-NCH$_2$), 2.18 (s, 3H, OAc), 1.54~1.42 (m, 4H, linker-CH$_2$), 1.39 (d, J=6.0 Hz, 3H, 6-H), 1.33~1.18 (m, 2H, linker-CH$_2$); $^{13}$C NMR (176 MHz, CDCl$_3$) δ: 207.1, 170.8, 170.4, 156.9, 156.3, 138.1, 138.0, 137.8, 137.0, 136.9, 135.9, 135.1, 133.4, 133.3, 133.2, 133.2, 133.1, 129.8, 128.7, 128.7, 128.6, 128.4, 128.4, 128.4, 128.3, 128.3, 128.3, 128.1, 128.1, 128.0, 128.0, 128.0, 127.9, 127.8, 127.8, 127.1, 126.9, 126.7, 126.4, 126.2, 126.2, 126.1, 126.0, 125.8, 98.9, 98.4, 97.1, 81.1, 80.3, 79.9, 75.6, 74.9, 73.9, 73.0, 72.9, 72.4, 72.2, 71.9, 71.8, 71.6, 69.6, 69.3, 69.0, 68.4, 67.3, 50.6, 50.3, 47.3, 46.3, 37.2, 32.1, 31.1, 30.2, 29.9, 29.6, 29.5, 29.3, 28.0, 27.6, 23.3, 22.8, 21.3, 21.1, 18.3, 18.2, 18.1, 14.3.

Compound 6: under protection of argon, the compound 26 (2.7 g, 3.7 mmol) is dissolved in methylene dichloride (20 mL), deionized water (10 mL), 2,3-dichloro-5,6-dicyan-1,4-benzoquinone (DDQ) (1.2 g, 5.5 mmol) are dropwise added in sequence, stirring is conducted for reaction for 10 hours at the room temperature. After complete reaction of raw materials is monitored by TLC, extraction with methylene dichloride is conducted, washing with a 10% (w/w) sodium thiosulfate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→7:3) to obtain a brown syrup 6 (1.9 g, 3.2 mmol, 86%). $R_f$=0.18 (PE:EA=7:3). $^1$H NMR (400 MHz, CDCl$_3$) δ: 7.42~7.12 (m, 15H, Ph), 5.59 (s, 1H, 2-H), 5.18 (d, J=11.5 Hz, 2H, Ph-CH$_2$), 4.78 (d, J=11.1 Hz, 1H, Ph-CH$_2$), 4.52~4.42 (m, 3H, 1-H, Ph-CH$_2$), 4.39 (d, J=11.1 Hz, 1H, Ph-CH$_2$), 3.91~3.70 (m, 1H, linker-OCH$_2$), 3.52 (td, J=9.3, 2.2 Hz, 1H, 4-H), 3.48~3.40 (m, 1H, linker-OCH), 3.38 (dd, J=9.2, 3.1 Hz, 1H, 3-H), 3.33 (dd, J=9.2, 6.1 Hz, 1H, 5-H), 3.30~3.15 (m, 2H, linker-NCH$_2$), 2.32 (d, J=2.2 Hz, 1H, 2-OH), 2.15 (s, 3H, OAc), 1.62~1.45 (m, 4H, linker-CH$_2$), 1.38 (d, J=6.1 Hz, 3H, 6-H), 1.34~1.20 (m, 2H, linker-CH$_2$); $^{13}$C NMR (101 MHz, CDCl$_3$) δ: 170.7, 170.5, 156.8, 156.3, 138.1, 137.4, 136.9, 128.8, 128.7, 128.6, 128.5, 128.4, 128.4, 128.3, 128.2, 128.1, 128.0, 127.9, 127.4, 98.9, 97.1, 79.9, 77.5, 77.4, 77.2, 76.8, 76.3, 73.1, 72.1, 71.7, 71.6, 71.3, 71.0, 70.1, 69.8, 68.7, 67.6, 67.3, 50.6, 50.3, 47.2, 46.3, 31.0, 29.3, 29.2, 28.0, 27.6, 23.3, 23.3, 21.2, 21.1, 18.1, 17.8.

Figure 5:
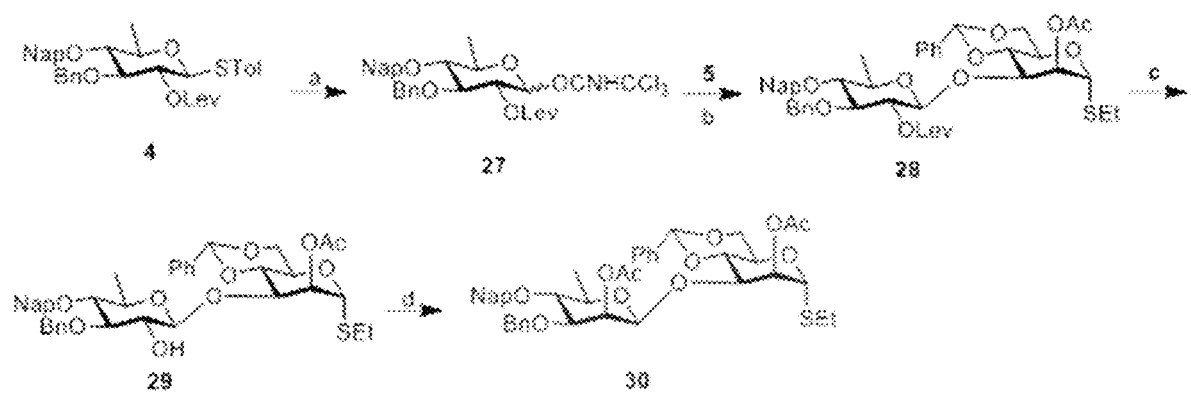

Example 5 synthesis of a carbohydrate building block 30 is shown in FIG. 5:

Specific experimental operation and steps:

Compound 28: the compound 4 (100 mg, 0.17 mmol) is dissolved in tetrahydrofuran (1 mL), deionized water (1 mL) is added, bromosuccinimide (72.6 mg, 0.41 mmol) is added, and stirring is conducted for reaction for 7 hours at the room temperature. After complete reaction of raw materials is monitored by TLC, extraction with methylene dichloride is conducted, washing with a 1 mmol·$L^{-1}$ saturated sodium bicarbonate solution and 10% (w/w) sodium thiosulfate is conducted, organic phases are collected, drying with anhydrous sodium sulfate is conducted, a solvent is removed through rotary evaporation to obtain an intermediate with hydroxyl at C-1 site, and a crude product is purified by silica gel column chromatography (PE:EA=10:1→1:1). The obtained compound is dissolved in methylene dichloride (1.5 mL), trichloroacetonitrile (300 μL) is added, 1,8-Diazabicyclo undec-7-ene (DBU) (15 μL) is added in an ice bath, and then stirring is conducted for reaction for 3 hours at the room temperature. After complete reaction of raw materials is monitored by TLC, a solvent is removed through rotary evaporation, and a crude product is purified by silica gel column chromatography (PE:EA=100:1→10:1 (1% triethylamine is added)) to obtain a compound 27 (84 mg, 0.13 mmol, 78% (total yield of the two-step reaction)). Under protection of argon, the compound 27 (84 mg, 0.13 mmol) and the compound 5 (92 mg, 0.26 mmol) are dissolved with methylbenzene, water is removed through rotary evaporation three times, the obtained mixture is placed on an oil pump overnight for vacuuming, a pre-activated 4 Å molecular sieve is added and dissolved in anhydrous methylene dichloride (1.5 mL), stirring is conducted for 15 minutes at −40° C., trimethylsilyl trifluoromethanesulfonate (3 μL) is added, and continuous stirring is conducted for 4 hours at −40° C. After complete reaction of raw materials is monitored by TLC, triethylamine (1 mL) is added for quenching the reaction, a solvent is removed through rotary evaporation, and a crude product is purified by silica gel column chromatography (PE:EA=20:1→3:1) to obtain a target disaccharide compound 28 (77 mg, 0.09 mmol, 72%). $R_f$=0.39 (PE:EA=7:3). $^1$H NMR (400 MHz, CDCl$_3$) δ: 8.16~6.87 (m, 17H, Ph), 5.60 (s, 1H, Ph-CH), 5.17 (d, J=1.5 Hz, 1H, Man1-H), 5.17~5.15 (m, 1H, Man2-H), 4.97 (dd, J=9.2, 7.6 Hz, 1H, Rha2-H), 4.92~4.60 (m, 4H, Ph-CH$_2$), 4.47 (d, J=7.7 Hz, 1H, Rha1-H), 4.20~4.14 (m, 2H, Man4-H, Man6-H), 4.10~4.03 (m, 2H, Man3-H, Man4-H), 3.87~3.79 (m, 1H, Man6'-H), 3.58 (t, J=9.0 Hz, 1H, Rha3-H), 3.41~3.33 (m, 1H, Rha5-H), 3.29 (t, J=9.1 Hz, 1H, Rha4-H), 2.74~2.43 (m, 6H, Lev-CH$_2$, SEt-CH$_2$), 2.11 (m, 6H, Lev-CH$_3$, OAc), 1.29~1.22 (m, 3H, SEt-CH$_3$) 1.21 (t, J=6.4 Hz, 3H, Rha6-H); $^{13}$C NMR (101 MHz, CDCl$_3$) δ: 206.5, 171.4, 171.4, 170.4, 138.3, 138.2, 138.1, 137.5, 137.5, 137.3, 135.7, 135.5, 134.3, 134.1, 133.4, 133.1, 132.2, 132.0, 130.3, 129.0, 129.0, 128.8, 128.5, 128.5, 128.4, 128.4, 128.3, 128.2, 128.1, 128.1, 128.1, 128.0, 127.8, 127.8, 127.8, 127.7, 127.6, 127.4, 127.3, 127.0, 126.9, 126.8, 126.7, 126.6, 126.5, 126.4, 126.3, 126.3, 126.2, 126.1, 125.8, 122.9, 122.7, 101.7, 101.6, 101.5, 83.6, 83.5, 83.4, 83.2, 82.9, 82.9, 82.9, 77.8, 77.4, 76.1, 76.0, 75.5, 75.3, 75.2, 75.0, 75.0, 74.9, 74.1, 72.8, 72.8, 71.8, 71.7, 71.7, 68.5, 64.9, 38.0, 30.0, 28.2, 25.7, 21.1, 18.0, 18.0, 18.0, 17.9, 15.1.

Compound 29: under protection of argon, the compound 28 (3.5 g, 4.2 mmol) is dissolved in methylene dichloride (30 mL), methanol (6 mL) is added, hydrazine acetate (581 mg, 6.3 mmol) is added, and stirring is conducted for reaction for 7 hours at the room temperature. After complete reaction of raw materials is monitored by TLC, a solvent is removed through rotary evaporation, and a crude product is purified by silica gel column chromatography (PE:EA=20:1→4:1) to obtain a syrup 29 (2.8 g, 3.9 mmol, 95%). $R_f$=0.38 (PE:EA=7:3). H NMR (400 MHz, CDCl$_3$) δ: 7.90~7.20 (m, 17H, Ph), 5.67 (s, 1H, Ph-CH), 5.46 (dd, J=3.2, 1.5 Hz, 1H, Man2-H), 5.27 (d, J=1.3 Hz, 1H, Man1-H), 5.14~4.92 (m, 2H, Ph-CH$_2$), 4.85~4.73 (m, 2H, Ph-CH$_2$), 4.40 (td, J=6.2, 2.6 Hz, 1H, Rha1-H), 4.34~4.21 (m, 3H, Man3-H, Man5-H, Man6-H), 4.09 (td, J=9.6, 3.0 Hz, 1H, Man4-H), 3.90 (m, 1H, Man6'-H), 3.66 (d, J=2.2 Hz, 1H, Rha2-OH), 3.63~3.56 (m, 2H, Rha2-H, Rha3-H), 3.47 (dt, J=9.1, 6.1 Hz, 1H, Rha5-H), 3.33~3.18 (m, 1H, Rha4-H), 2.65 (m, 3H, SEt-CH$_2$), 2.21 (s, 3H, OAc), 1.37~1.25 (m, 6H, SEt-CH$_3$, Rha6-H); $^{13}$C NMR (101 MHz, CDCl$_3$) δ: 171.4, 138.9, 138.8, 137.7, 137.2, 137.2, 136.2, 134.4, 134.1, 132.3, 132.0, 130.3, 129.2, 128.7, 128.5, 128.5, 128.4, 128.2, 128.2, 128.2, 128.2, 128.1, 127.8, 127.8, 127.7, 127.7, 127.7, 127.6, 127.5, 127.4, 127.3, 126.9, 126.8, 126.6, 126.5, 126.3, 126.3, 126.2, 126.2, 126.0, 125.9, 123.0, 122.5, 104.8, 104.7, 101.8, 84.2, 84.2, 84.1, 83.6, 83.3, 83.2, 82.9, 77.6, 77.4, 75.8, 75.7, 75.5, 75.4, 75.3, 75.3, 75.2, 75.2, 74.4, 73.9, 73.9, 72.0, 72.0, 68.6, 65.0, 25.6, 21.4, 18.3, 18.3, 18.2, 18.2, 15.0.

Compound 30: under protection of argon, oxalyl chloride (1 mL, 50 mmol) is dissolved in anhydrous methylene dichloride (13 mL), and stirring is conducted at −78° C. Under protection of argon, dimethylsulfoxide (1.7 mL, 22 mmol) is dissolved in anhydrous methylene dichloride (4.5 mL) through dropwise adding, and stirring is conducted for reaction for 1 hour at −78° C. after dropwise adding is completed. A carbohydrate building block 29 (1.6 g, 2.2 mmol) is dissolved in anhydrous methylene dichloride (14 mL), the mixture is dropwise added into a reaction system under protection of argon, and stirring is conducted for reaction for 0.5 hour at −78° C. after dropwise adding is completed. Then, under protection of argon, triethylamine (3.1 mL, 22 mmol) is dropwise added, a white solid slowly appears, and stirring is conducted for reaction for 3 hours at −78° C. after dropwise adding is completed. After complete reaction of raw materials is monitored by TLC, extraction with methylene dichloride is conducted, washing with a 10% (w/w) sodium thiosulfate solution is conducted, organic phases are collected, dewatering and drying with anhydrous sodium sulfate are conducted, a solvent is removed through filtration and spin-drying, and a product is directly used for next step reaction without separation and purification. A crude product and methylbenzene are subjected to azeotropic dewatering three times, under protection of argon, the obtained mixture is dissolved in absolute ethyl alcohol (16 mL), the temperature is cooled to 0° C., sodium borohydride (125 mg, 3.3 mmol) is added, and stirring is conducted for reaction for 30 hour at 0° C. After complete reaction of raw materials is monitored by TLC, an insoluble substance is filtered out, washing with a saturated sodium chloride solution is conducted, organic phases are collected, dewatering and drying with anhydrous sodium sulfate are conducted, a solvent is removed through filtration and spin-drying, and a crude product is purified by silica gel column chromatography (PE:EA=10:1→4:1) to obtain a syrup. A product is dissolved in dry pyridine (11 mL), the temperature is cooled to 0° C., hydrazine acetate (1 mL) is dropwise added, dimethylformamide (DMAP) (54 mg, 0.44 mmol) is added, reaction is conducted for 30 minutes under an ice bath, the temperature is raised to the room temperature, and stirring is conducted for reaction for 10 hours. After complete reaction of raw materials is monitored by TLC, extraction with methylene dichloride is conducted, sequential washing with 1 mmol·L$^{-1}$ hydrochloric acid and a saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→3:1) to obtain brown syrup 30 (1.5 g, 1.9 mmol, 88%). $R_f$=0.38 (PE:EA=7:3). $^1$H NMR (400 MHz, CDCl$_3$) δ: 8.35~7.20 (m, 17H, Ph), 5.59 (d, J=1.8 Hz, 1H, Ph-CH), 5.52 (d, J=2.8 Hz, 1H, Rha2-H), 5.39 (dt, J=3.7, 2.0 Hz, 1H, Man2-H), 5.24 (d, J=1.5 Hz, 1H, Man1-H), 5.23~4.68 (m, 4H, Rha1-H, Ph-CH$_2$), 4.47 (dd, J=13.7, 11.1 Hz, 1H, Ph-CH$_2$), 4.33~4.18 (m, 3H, Man3-H, Man5-H, Man6-H), 4.04 (t, J=9.7 Hz, 1H, Man4-H), 3.92~3.83 (m, 1H, Man6'-H), 3.63 (ddd, J=8.9, 5.3, 3.3 Hz, 1H, Rha3-H), 3.53~3.42 (m, 1H, Rha4-H), 3.37 (m, 1H, Rha5-H), 2.74~2.50 (m, 2H, SEt-CH$_2$), 2.19 (s, 3H, OAc), 2.07 (s, 3H, OAc), 1.39~1.36 (m, 3H, Rha6-H), 1.30 (td, J=7.4, 0.9 Hz, $^{13}$H, SEt-CH$_3$); $^{13}$C NMR (101 MHz, CDCl$_3$) δ:170.8, 170.4, 170.4, 137.9, 137.8, 137.8, 137.7, 137.6, 136.3, 136.0, 134.3, 134.1, 133.4, 133.1, 132.3, 132.0, 130.3, 130.0, 129.1, 128.7, 128.6, 128.5, 128.5, 128.4, 128.3, 128.3, 128.3, 128.2, 128.2, 128.0, 127.9, 127.9, 127.8, 127.8, 127.7, 127.5, 127.4, 127.3, 127.1, 127.0, 126.8, 126.8, 126.6, 126.6, 126.5, 126.3, 126.2, 126.0, 125.9, 123.0, 122.6, 101.8, 96.7, 96.7, 96.7, 83.6, 80.2, 80.2, 80.1, 80.0, 79.9, 79.8, 79.7, 78.1, 78.0, 77.4, 75.5, 75.3, 75.2, 74.9, 72.2, 72.2, 72.1, 71.6, 71.6, 71.5, 71.3, 71.2, 68.7, 68.0, 67.9, 67.9, 64.7, 31.0, 25.7, 21.2, 21.1, 21.1, 18.2, 18.1, 18.1, 15.0.

Figure 6:
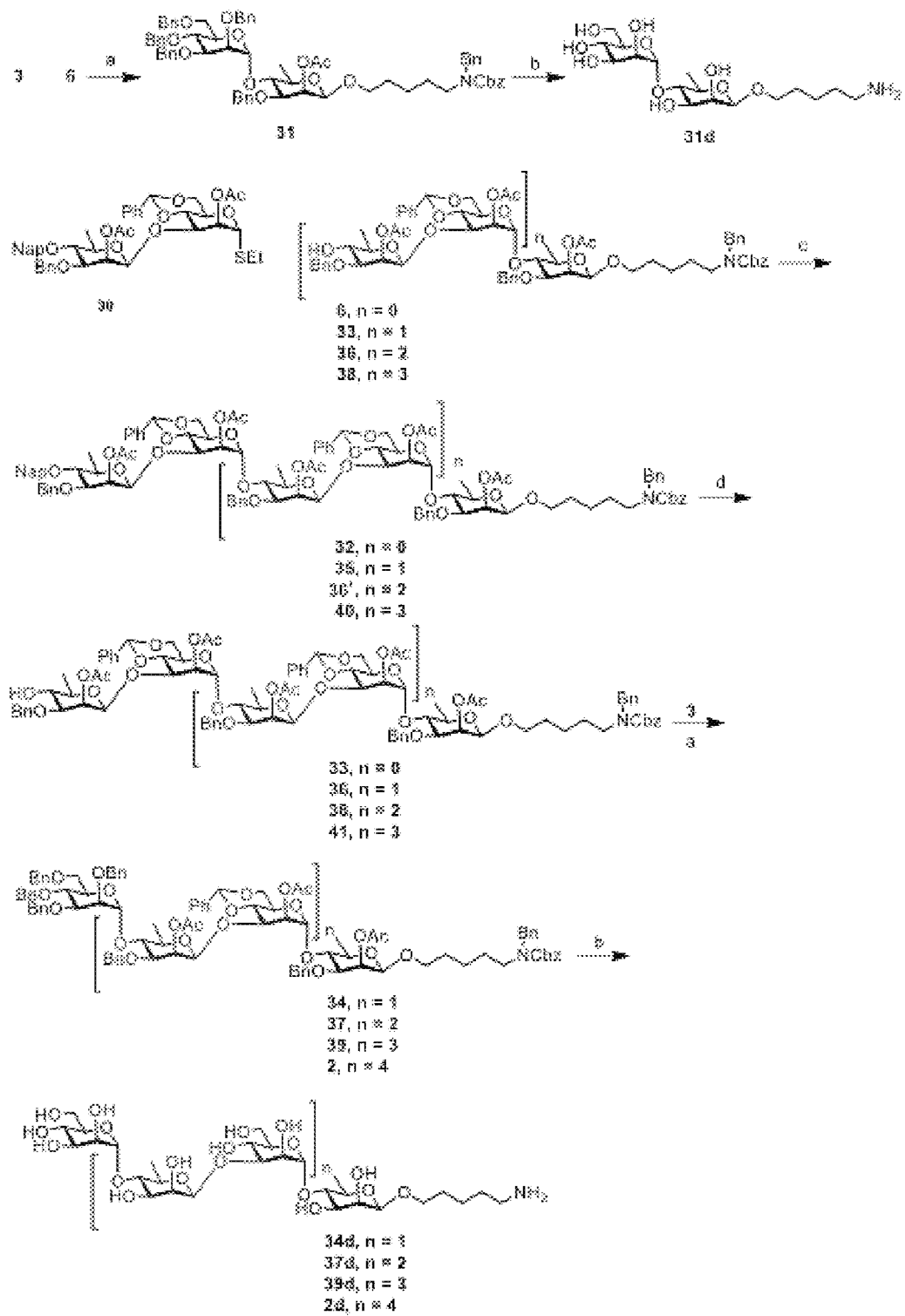

Example 6 synthesis of an oligosaccharide fragment is shown in FIG. 6.

Specific experimental operation and steps:

Compound 31: under protection of argon, the compound 3 (86.6 mg, 0.15 mmol) and the compound 6 (59.8 mg, 0.1 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (1 mL) and anhydrous ether (1 mL) are added, iodosuccinimide (26.7 mg, 0.12 mmol) is added, the temperature is cooled to 0° C., stirring is conducted for 30 minutes, trimethylsilyl trifluoromethanesulfonate (3.6 μL) is dropwise added, and stirring is conducted for reaction for 5 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→4:1) to obtain a syrup 31 (89.5 mg, 0.08 mmol, 80%). $R_f$=0.44 (PE:EA=7:3). $^1$H NMR (400 MHz, CDCl$_3$) δ: 7.40~7.10 (m, 35H, Ph), 5.58 (s, 1H, Rha2-H), 5.31 (d, J=2.0 Hz, 1H, Man1-H), 5.20~5.11 (m, 2H, Ph-CH$_2$), 4.87~4.35 (m, 10H, R$_1$-H, Ph-CH$_2$), 4.30~4.16 (m, 3H, Ph-CH$_2$), 4.01 (t, J=9.5 Hz, 1H, Man5-H), 3.90~3.73 (m, 4H, Man3-H, Man4-H, Man6-H), 3.71~3.62 (m, 3H, Man2-H, Rha4-H, linker-OCH), 3.47 (dd, J=9.3, 2.9 Hz, 1H, Rha3-H), 3.40 (d, J=18.3 Hz, 1H, linker-OCH), 3.31 (dd, J=9.2, 6.1 Hz, 1H, Rha4-H), 3.22 (d, J=23.8 Hz, 2H, linker-NCH$_2$), 2.15 (s, 3H, OAc), 1.53 (s, 4H, linker-CH$_2$), 1.39 (d, J=6.1 Hz, 3H, Rha6-H), 1.32~1.19 (m, 2H, linker-CH$_2$); $^{13}$C NMR (101 MHz, CDCl$_3$) δ: 170.6, 156.8, 156.3, 138.9, 138.8, 138.5, 138.5, 138.1, 137.5, 137.0, 128.6, 128.5, 128.5, 128.4, 128.4, 128.3, 128.2, 128.2, 128.1, 128.0, 127.9, 127.9, 127.9, 127.8, 127.8, 127.7, 127.6, 127.6, 127.5, 127.9, 127.9, 127.8, 127.8, 127.7, 127.6, 127.6, 127.5, 127.4, 127.2, 100.3, 100.0, 98.7, 98.4, 95.4, 80.7, 80.2, 79.9, 78.7, 77.4, 76.4, 76.1, 75.2, 74.9, 74.6, 74.5, 74.2, 73.5, 72.9, 72.5, 72.1, 72.0, 71.5, 71.4, 71.1, 69.8, 69.3, 69.1, 67.6, 67.3, 65.1, 50.6, 50.3, 47.2, 46.3, 29.8, 29.2, 28.0, 27.6, 23.3, 21.1, 21.0, 18.6.

Compound 32: under protection of argon, the compound 30 (286.6 mg, 0.37 mmol) and the compound 6 (187.2 mg, 0.31 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (5 mL) is added, iodosuccinimide (104.6 mg, 0.47 mmol) is added, the temperature is cooled to 0° C., stirring is conducted for 30 minutes, trimethylsilyl trifluoromethanesulfonate (12 μL) is dropwise added, and stirring is conducted for reaction for 6 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20: 1→3:1) to obtain a syrup 32 (257.1 mg, 0.20 mmol, 63%). $R_f$=0.21 (PE:EA=7:3). $^1$H NMR (400 MHz, CDCl$_3$) δ: 8.35~7.12 (m, 32H, Ph), 5.60 (s, 1H, Rha2c-H), 5.57 (s, 1H, Ph-CH), 5.52 (d, J=2.9 Hz, 1H, Rha2a-H), 5.42 (td, J=3.2, 1.5 Hz, 1H, Man2-H), 5.30 (d, J=1.5 Hz, 1H, Man1-H), 5.25~4.65 (m, 8H, Rha1a-H, Ph-CH$_2$), 4.55~4.35 (m, 4H, Rha1c-H, Ph-CH$_2$), 4.24~4.15 (m, 2H, Man3-H, Man6-H), 3.99~3.88 (m, 2H, Man4-H, linker-OCH), 3.80 (t, J=9.7 Hz, 2H, Man5-H, Man6'-H), 3.70~3.55 (m, 3H, Rha3a-H, Rha3c-H, linker-OCH), 3.53~3.30 (m, 4H, Rha4a-H, Rha4c-H, Rha5a-H, Rha5c-H), 3.30~3.13 (m, 2H, linker-NCH$_2$), 2.12 (s, 3H, OAc), 2.09 (s, 3H, OAc), 1.63~1.45 (m, 4H, linker-CH$_2$), 1.43~1.37 (m, 6H, Rha6a-H, Rha6c-H), 1.36~1.17 (m, 2H, linker-CH$_2$); $^{13}$C NMR (101 MHz, CDCl$_3$) δ: 170.9, 170.8, 170.6, 170.5, 170.0, 170.0, 156.8, 156.3, 138.1, 137.9, 137.8, 137.7, 137.6, 137.5, 137.0, 136.2, 136.0, 134.3, 134.1, 133.4, 133.1, 132.3, 130.3, 130.0, 129.0, 129.0, 128.8, 128.8, 128.7, 128.7, 128.6, 128.5, 128.5, 128.5, 128.4, 128.3, 128.3, 128.2, 128.2, 128.1, 128.1, 128.0, 128.0, 127.9, 127.9, 127.8, 127.8, 127.7, 127.5, 127.5, 127.4, 127.3, 127.0, 126.8, 126.8, 126.7, 126.6, 126.3, 126.2, 126.0, 125.9, 122.9, 122.7, 101.5, 100.2, 98.8, 98.4, 96.6, 96.5, 80.2, 80.1, 80.0, 79.8, 79.7, 78.3, 77.4, 75.7, 75.5, 75.2, 73.2, 72.1, 72.0, 72.0, 71.9, 71.4, 71.3, 71.2, 70.9, 70.9, 69.8, 69.1, 69.1, 68.6, 68.0, 67.9, 67.6, 67.3, 64.8, 50.6, 50.4, 47.2, 46.3, 29.4, 29.2, 28.0, 27.6, 23.3, 21.1, 21.1, 21.1, 21.0, 20.9, 18.7, 18.2, 18.2, 18.2, 17.8.

Compound 33: under protection of argon, the compound 32 (61.7 mg, 0.047 mmol) is dissolved in methylene dichloride (1 mL), deionized water (0.5 mL), 2,3-dichloro-5,6-dicyan-1,4-benzoquinone (DDQ) (15.7 mg, 0.07 mmol) are dropwise added in sequence, and stirring is conducted for reaction for 5 hours at the room temperature. After complete reaction of raw materials is monitored by TLC, extraction with methylene dichloride is conducted, washing with a 10% (w/w) sodium thiosulfate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→1:1) to obtain a brown syrup 33

(38.5 mg, 0.033 mmol, 70%). R$_f$=0.21 (PE:EA=3:2). $^1$H NMR (400 MHz, CDCl$_3$) δ: 7.58~7.12 (m, 25H, Ph), 5.61 (d, J=3.1 Hz, 1H, Rha2c-H), 5.58 (s, 1H, Ph-CH), 5.49 (d, J=3.1 Hz, 1H, Rha2a-H), 5.42 (dd, J=3.6, 1.2 Hz, 1H, Man2-H), 5.31 (d, J=1.5 Hz, 1H, Man1-H), 5.25~4.65 (m, 5H, Rha1a-H, Ph-CH$_2$), 4.55~4.35 (m, 5H, Rha1c-H, Ph-CH$_2$), 4.24~4.10 (m, 2H, Man3-H, Man6-H), 3.99~3.88 (m, 2H, Man4-H, linker-OCH), 3.85~3.77 (m, 2H, Man5-H, Man6'-H), 3.68~3.55 (m, 2H, Rha3c-H, linker-OCH), 3.55~3.30 (m, 4H, Rha3c-H, Rha4a-H, Rha4c-H, Rha5a-H), 3.30~3.13 (m, 3H, Rha5c-H, linker-NCH$_2$), 2.25 (d, J=2.2 Hz, 1H, Rha4a-OH), 2.13 (s, 3H, OAc), 2.09 (s, 3H, OAc), 2.06 (s, 3H, OAc), 1.63~1.45 (m, 4H, linker-CH$_2$), 1.41 (d, J=6.1 Hz, 1H, Rha6a-H), 1.35 (d, J=6.1 Hz, 1H, Rha6c-H), 1.33~1.20 (m, 2H, linker-CH$_2$); $^{13}$C NMR (101 MHz, CDCl$_3$) δ: 170.8, 170.6, 170.0, 156.3, 138.1, 137.6, 137.5, 137.0, 129.0, 128.9, 128.7, 128.7, 128.6, 128.5, 128.4, 128.2, 128.1, 128.0, 128.0, 127.4, 126.2, 101.5, 100.2, 98.8, 96.6, 80.1, 79.7, 77.6, 77.4, 72.3, 72.0, 71.5, 71.2, 71.1, 70.9, 69.8, 69.1, 68.6, 67.7, 67.3, 67.2, 64.8, 50.6, 50.4, 47.3, 46.3, 29.3, 28.0, 27.6, 23.3, 21.1, 21.0, 21.0, 18.7, 17.8.

Compound 34: under protection of argon, the compound 33 (38.5 mg, 0.033 mmol) and the compound 3 (28.7 mg, 0.049 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (1 mL) and anhydrous ether (1 mL) are added, iodosuccinimide (8.9 mg, 0.04 mmol) is added, the temperature is cooled to 0° C., stirring is conducted for 30 minutes, trimethylsilyl trifluoromethanesulfonate (1.2 μL) is dropwise added, and stirring is conducted for reaction for 5 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→7:3) to obtain a syrup 34 (29.5 mg, 0.017 mmol, 53%). R$_f$=0.43 (PE:EA=3:2). $^1$H NMR (400 MHz, CDCl$_3$) δ: 7.58~7.05 (m, 45H, Ph), 5.62 (s, 1H, Rha2d-H), 5.58 (s, 1H, Ph-CH), 5.49 (d, J=3.1 Hz, 1H, Rha2b-H), 5.42 (dd, J=3.6, 1.2 Hz, 1H, Man2c-H), 5.31 (d, J=1.5 Hz, 1H, Mania-H, Man1c-H), 5.25~4.10 (m, 20H, Rha1b-H, Rha1d-H, Ph-CH$_2$), 4.30~4.10 (m, 6H, Man3c-H, Man6c-H), 4.05~3.76 (m, 10H), 3.75~3.58 (m, 7H), 3.52~3.35 (m, 3H, Rha5b-H), 3.32~3.15 (m, 4H, Rha5d-H, linker-NCH$_2$), 2.14 (s, 3H, OAc), 2.09 (s, 3H, OAc), 2.07 (s, 3H, OAc), 1.63~1.45 (m, 4H, linker-CH$_2$), 1.42 (d, J=6.1 Hz, 3H, Rha6b-H), 1.37 (d, J=6.1 Hz, 3H, Rha6d-H), 1.34~1.20 (m, 2H, linker-CH$_2$); $^{13}$C NMR (151 MHz, CDCl$_3$) δ: 207.0, 192.5, 170.8, 170.6, 170.6, 170.2, 170.1, 170.0, 156.3, 138.9, 138.8, 138.8, 138.8, 138.6, 138.5, 138.5, 138.4, 138.1, 137.5, 137.3, 137.0, 134.6, 129.9, 129.1, 129.0, 128.7, 128.7, 128.6, 128.5, 128.5, 128.4, 128.4, 128.3, 128.3, 128.2, 128.1, 128.1, 128.0, 127.9, 127.9, 127.8, 127.8, 127.8, 127.7, 127.7, 127.6, 127.5, 127.3, 127.2, 126.3, 126.1, 101.4, 100.2, 100.1, 100.0, 99.5, 98.7, 96.9, 96.2, 80.4, 80.2, 80.2, 80.1, 79.9, 78.7, 78.4, 77.9, 77.6, 77.4, 77.2, 77.2, 76.9, 76.0, 75.3, 75.0, 73.5, 73.0, 72.9, 72.6, 72.1, 72.1, 72.0, 71.8, 71.6, 71.5, 71.2, 71.1, 71.0, 70.9, 70.8, 69.8, 69.4, 69.4, 68.9, 68.6, 68.6, 67.6, 67.3, 67.2, 67.2, 66.2, 64.8, 62.6, 50.6, 50.3, 47.2, 46.3, 31.1, 29.2, 28.1, 28.0, 27.6, 23.3, 21.1, 21.0, 21.0, 20.7, 18.9, 18.7, 18.6, 18.5.

Compound 35: under protection of argon, the compound 30 (488.6 mg, 0.63 mmol) and the compound 33 (619.7 mg, 0.53 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (10 mL) is added, iodosuccinimide (179 mg, 0.8 mmol) is added, the temperature is cooled to 0° C., stirring is conducted for 30 minutes, trimethylsilyl trifluoromethanesulfonate (23.6 μL) is dropwise added, stirring is conducted for reaction for 5 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→7:3) to obtain a syrup 35 (720.2 mg, 0.38 mmol, 72%). R$_f$=0.44 (PE:EA=3:2). $^1$H NMR (400 MHz, CDCl$_3$) δ: 8.35~7.05 (m, 42H, Ph), 5.60 (s, 1H, Rha2e-H), 5.58 (s, 1H, Ph-CH), 5.56 (s, 1H, Ph-CH), 5.52 (d, J=2.2 Hz, 1H, Rha2a-H), 5.48 (d, J=2.6 Hz, 1H, Rha2c-H), 5.41 (dd, J=3.8, 1.9 Hz, 2H, Man2b-H, Man2d-H), 5.28 (d, J=2.0 Hz, 2H, Man1b-H, Man1d-H), 5.25~4.62 (m, 9H, Rha1a-H, Rha1c-H, Ph-CH$_2$), 4.56~4.34 (m, 6H, Rha1e-H, Ph-CH$_2$), 4.26~4.12 (m, 4H, Man3b-H, Man3d-H, Man6b-H, Man6d-H), 3.99~3.85 (m, 4H, Man4b-H, Man4d-H, linker-OCH$_2$), 3.84~3.72 (m, 3H), 3.70~3.34 (m, 9H), 3.31 (dd, J=7.9, 6.2 Hz), 3.28~3.12 (m, 2H, linker-NCH$_2$), 2.12 (s, 3H, OAc), 2.10 (s, 3H, OAc), 2.09 (s, 3H, OAc), 2.09 (s, 3H, OAc), 2.03 (s, 3H, OAc), 1.63~1.45 (m, 4H, linker-CH$_2$), 1.43~1.33 (m, 9H, Rha6-H), 1.34~1.20 (m, 2H, linker-CH$_2$); $^{13}$C NMR (101 MHz, CDCl$_3$) δ: 177.1, 170.9, 170.7, 170.6, 170.1, 170.0, 138.1, 137.9, 137.7, 137.5, 137.5, 137.0, 137.0, 136.2, 136.0, 134.1, 133.4, 133.1, 132.3, 132.0, 130.3, 129.1, 129.0, 128.9, 128.7, 128.6, 128.6, 128.5, 128.3, 128.3, 128.3, 128.2, 128.2, 128.1, 128.0, 128.0, 127.9, 127.8, 127.8, 127.7, 127.5, 127.4, 127.3, 126.9, 126.8, 126.7, 126.6, 126.2, 126.2, 126.0, 125.8, 122.9, 122.6, 101.6, 101.5, 100.3, 100.2, 100.1, 98.8, 96.4, 96.3, 96.1, 80.2, 80.2, 80.0, 79.7, 79.5, 77.7, 77.4, 77.3, 75.5, 75.3, 75.2, 72.1, 72.0, 71.9, 71.5, 71.4, 71.2, 71.0, 70.9, 70.9, 69.8, 69.1, 68.8, 68.6, 68.0, 67.9, 67.6, 67.3, 64.8, 50.6, 50.4, 47.2, 46.3, 29.7, 29.2, 28.0, 27.6, 23.3, 21.1, 21.1, 21.0, 21.0, 20.9, 18.7, 18.7, 18.2, 18.2, 18.2.

Compound 36: under protection of argon, the compound 35 (45.4 mg, 0.024 mmol) is dissolved in methylene dichloride (1 mL), deionized water (0.5 mL), 2,3-dichloro-5,6-dicyan-1,4-benzoquinone (DDQ) (8 mg, 0.036 mmol) are dropwise added in sequence, and stirring is conducted for reaction for 10 hours at the room temperature. After complete reaction of raw materials is monitored by TLC, extraction with methylene dichloride is conducted, washing with a 10% (w/w) sodium thiosulfate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→1:1) to obtain a brown syrup 33 (20.2 mg, 0.012 mmol, 50%). R$_f$=0.22 (PE:EA=3:2). $^1$H NMR (400 MHz, CDCl$_3$) δ: 7.53~7.10 (m, 35H, Ph), 5.61 (s, 1H, Rha2e-H), 5.57 (s, 1H, Ph-CH), 5.56 (s, 1H, Ph-CH), 5.49 (d, J=3.6 Hz, 2H, Rha2a-H, Rha2c-H), 5.40 (dd, J=3.6, 1.6 Hz, 2H, Man2b-H, Man2d-H), 5.29 (d, J=1.6 Hz, 1H, Man1d-H), 5.28 (d, J=1.6 Hz, 1H, Man1b-H), 5.17 (d, J=10.8 Hz, 2H, Ph-CH$_2$), 4.78~4.62 (m, 5H, Rha1a-H, Rha1c-H, Ph-CH$_2$), 4.53~4.33 (m, 7H, Rha1e-H, Ph-CH$_2$), 4.26~4.12 (m, 4H, Man3b-H, Man3d-H, Man6b-H, Man6d-H), 3.99~3.85 (m, 4H, Man4b-H, Man4d-H, linker-OCH$_2$), 3.84~3.72 (m, 3H), 3.70~3.34 (m, 12H), 3.35~3.12 (m, 4H, Rha5-H, linker-NCH$_2$), 2.12 (s, 3H, OAc), 2.10 (s, 3H, OAc), 2.09 (s, 3H, OAc), 2.06 (s, 3H, OAc), 2.03 (s, 3H, OAc), 1.63~1.45 (m, 4H, linker-CH$_2$), 1.41 (d, J=6.1 Hz, 3H, Rha6e-H), 1.36 (d, J=6.1 Hz, 6H, Rha6a-H, Rha6c-H), 1.34~1.20 (m, 2H, linker-CH$_2$); $^{13}$C NMR (101 MHz, CDCl$_3$) δ: 170.8, 170.7, 170.7, 170.6, 170.6, 170.2, 170.1, 170.1, 138.1, 137.5, 137.4, 137.0, 137.0, 129.1, 129.0, 128.9, 128.9, 128.7, 128.7, 128.6, 128.6, 128.4, 128.4, 128.3, 128.1, 128.0, 128.0, 127.4, 126.2, 126.2, 101.6, 101.5, 100.3, 100.2, 98.8, 96.4, 96.1, 80.2, 79.7, 79.5, 77.7, 77.6, 77.4, 72.4, 71.9, 71.5, 71.2, 71.0, 70.9, 70.9, 69.8, 69.0, 68.8, 68.6, 67.6, 67.3, 67.3, 67.2, 64.8, 50.6, 50.4, 47.2, 46.3, 29.3, 28.0, 27.6, 23.3, 21.1, 21.0, 21.0, 21.0, 20.9, 18.7, 18.7, 17.8.

Compound 37: under protection of argon, the compound 36 (20.2 mg, 0.012 mmol) and the compound 3 (33.8 mg, 0.058 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (1 mL) and anhydrous ether (1 mL) are added, iodosuccinimide (13.5 mg, 0.06 mmol) is added, the temperature is cooled to 0° C., stirring is conducted for 30 minutes, trimethylsilyl trifluoromethane-sulfonate (0.5 μL) is dropwise added, and stirring is conducted for reaction for 8 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→2:1) to obtain a syrup 37 (21.1 mg, 0.009 mmol, 78%). R$_f$=0.32 (PE:EA=3: 2). 1H NMR (700 MHz, CDCl3) δ: 7.53~7.10 (m, 55H, Ph), 5.60 (s, 1H, Rha2f-H), 5.57 (s, 1H, Ph-CH), 5.56 (s, 1H, Ph-CH), 5.48 (d, J=3.2 Hz, 2H, Rha2b-H, Rha2d-H), 5.40 (d, J=3.8 Hz, 2H, Man2c-H, Man2e-H), 5.30 (d, J=2.1 Hz, 1H, Man1e-H), 5.29 (d, J=1.4 Hz, 1H, Man1c-H), 5.27 (d, J=1.5 Hz, 1H, Mania-H), 5.17 (d, J=11.2 Hz, 2H, Ph-CH2), 4.84 (d, J=10.6 Hz, 1H, Ph-CH2), 4.75~4.58 (m, 10H), 4.55~4.35 (m, 8H), 4.30~4.10 (m, 9H), 4.00 (d, J=9.5 Hz, 1H), 3.95~3.75 (m, 12H), 3.73~3.55 (m, 9H), 3.51-3.35 (m, 4H), 3.32~3.20 (m, 4H), 3.19 (s, 1H, linker-NCH2), 2.12 (s, 3H, OAc), 2.09 (s, 3H, OAc), 2.08 (s, 3H, OAc), 2.06 (s, 3H, OAc), 2.03 (s, 3H, OAc), 1.63~1.45 (m, 4H, linker-CH2), 1.45~1.33 (m, 9H, Rha6-H), 1.34~1.20 (m, 2H, linker-CH2); 13C NMR (176 MHz, CDCl3) δ: 170.6, 170.5, 170.0, 138.7, 138.4, 137.4, 136.9, 128.9, 128.7, 128.6, 128.5, 128.5, 128.4, 128.4, 128.3, 128.2, 128.2, 128.1, 128.0, 127.9, 127.8, 127.7, 127.7, 127.6, 127.4, 127.1, 126.1, 126.0, 101.5, 101.3, 100.1, 99.8, 98.6, 95.9, 80.1, 79.8, 78.5, 77.2, 77.0, 76.8, 75.9, 75.2, 74.8, 73.4, 72.8, 72.0, 71.8, 71.6, 71.3, 71.1, 70.9, 70.8, 70.7, 69.3, 68.8, 68.7, 68.4, 67.5, 67.1, 64.6, 53.4, 31.6, 29.1, 29.1, 23.2, 22.7, 21.0, 20.9, 20.9, 20.8, 18.6, 18.5, 18.5, 14.2, 14.1, 11.4.

Compound 38: under protection of argon, the compound 30 (119.1 mg, 0.15 mmol) and the compound 36 (134.6 mg, 0.077 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (5 mL) is added, iodosuccinimide (39.8 mg, 0.18 mmol) is added, the temperature is cooled to 0° C., stirring is conducted for 30 minutes, trimethylsilyl trifluoromethanesulfonate (5 μL) is dropwise added, and stirring reaction is conducted for 10 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, extraction with methylene dichloride is conducted, washing with the saturated sodium bicarbonate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→2:1) to obtain a syrup 38 (127.6 mg, 0.052 mmol, 67%). R$_f$=0.58 (PE:EA=1:1). $^1$H NMR (400 MHz, CDCl$_3$) δ: 8.35~7.10 (m, 52H, Ph), 5.60 (s, 1H, Rha2g-H), 5.58 (s, 1H, Ph-CH), 5.56 (s, 2H, Ph-CH), 5.53 (d, J=2.9 Hz, 1H, Rha2a-H), 5.49 (d, J=2.4 Hz, 2H, Rha2c-H, Rha2e-H), 5.40 (m, 3H, Man2-H), 5.29 (d, J=1.5 Hz, 2H, Man1d-H, Man1f-H), 5.27 (d, J=1.5 Hz, 1H, Man1b-H), 5.18 (m, 2H, Ph-CH2), 4.80~4.62 (m, 7H, Rha1a-H, Rha1c-H, Rha1e-H, Ph-CH2), 4.55~4.33 (m, 7H, Rha1g-H, Ph-CH2), 4.28~4.18 (m, 6H, Man3-H, Man6-H), 4.05~3.85 (m, 6H, Man4-H, linker-OCH$_2$), 3.84~3.73 (m, 6H), 3.70~3.55 (m, 8H), 3.55~3.12 (m, 10H, Rha5-H, linker-NCH$_2$), 2.13~2.00 (m, 21H, 7OAc), 1.63~1.45 (m, 4H, linker-CH2), 1.43~1.33 (m, 12H, Rha6-H), 1.33~1.18 (m, 2H, linker-CH2); $^{13}$C NMR (101 MHz, CDCl$_3$) δ: 177.2, 170.9, 170.7, 170.6, 170.1, 170.1, 170.1, 138.1, 137.9, 137.8, 137.7, 137.5, 137.5, 137.1, 137.0, 136.2, 136.0, 134.3, 134.1, 133.4, 133.1, 132.3, 131.0, 130.3, 129.1, 129.0, 129.0, 128.9, 128.8, 128.6, 128.6, 128.5, 128.5, 128.3, 128.3, 128.3, 128.3, 128.2, 128.2, 128.1, 128.0, 127.9, 127.9, 127.8, 127.7, 127.5, 127.4, 127.3, 126.9, 126.8, 126.6, 126.6, 126.2, 126.2, 126.0, 125.8, 122.9, 122.6, 101.6, 101.6, 100.2, 98.8, 96.4, 96.3, 96.0, 95.9, 93.7, 80.2, 80.2, 80.1, 80.0, 79.7, 79.7, 79.5, 77.8, 77.6, 77.4, 75.5, 75.2, 72.1, 72.0, 71.9, 71.8, 71.4, 71.3, 71.2, 71.0, 70.9, 69.8, 69.0, 68.8, 68.7, 68.6, 68.0, 67.9, 67.6, 67.3, 65.7, 64.7, 50.4, 47.2, 46.3, 30.7, 29.7, 29.3, 28.0, 23.3, 21.1, 21.0, 20.9, 19.3, 18.7, 18.7, 18.6, 18.2, 18.1, 13.8.

Compound 39: under protection of argon, the compound 38 (127.6 mg, 0.052 mmol) is dissolved in methylene dichloride (2 mL), deionized water (0.5 mL), 2,3-dichloro-5,6-dicyan-1,4-benzoquinone (DDQ) (17.4 mg, 0.078 mmol) are dropwise added in sequence, and stirring is conducted for reaction for 9 hours at the room temperature. After complete reaction of raw materials is monitored by TLC, extraction with methylene dichloride is conducted, washing with a 10% (w/w) sodium thiosulfate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→3:2) to obtain a brown syrup 39 (78.5 mg, 0.034 mmol, 65%). R$_f$=0.42 (PE:EA=1:1). $^1$H NMR (400 MHz, CDCl$_3$) δ: 7.53~7.12 (m, 45H, Ph), 5.60 (s, 1H, Rha2g-H), 5.58 (s, 1H, Ph-CH), 5.57 (s, 1H, Ph-CH), 5.56 (s, 1H, Ph-CH), 5.49 (m, 3H, Rha2-H), 5.43~5.38 (m, 3H, Man2-H), 5.31~5.25 (m, 3H, Man1-H), 5.21~5.12 (m, 2H, Ph-CH2), 4.78~4.62 (m, 7H, Rha1-H, Ph-CH2), 4.53~4.34 (m, 7H, Rha1g-H, Ph-CH2), 4.26~4.13 (m, 6H, Man3-H, Man6-H), 4.05~3.86 (m, 6H, Man4-H, linker-OCH$_2$), 3.85~3.73 (m, 5H, Man5-H), 3.68~3.55 (m, 6H, Rha3-H), 3.55~3.12 (m, 10H, Rha5-H, linker-NCH$_2$), 2.27 (d, J=2.1 Hz, 1H, Rha4a-OH), 2.12 (s, 3H, OAc), 2.10 (s, 6H, OAc), 2.09 (s, 3H, OAc), 2.06 (s, 3H, OAc), 2.04 (s, 3H, OAc), 2.03 (s, 3H, OAc), 1.63~1.45 (m, 4H, linker-CH2), 1.43~1.33 (m, 12H, Rha6-H), 1.33~1.18 (m, 2H, linker-CH2).

Compound 40: under protection of argon, the compound 39 (16.1 mg, 0.007 mmol) and the compound 3 (20.3 mg, 0.035 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (1 mL) and anhydrous ether (1 mL) are added, iodosuccinimide (7.9 mg, 0.035 mmol) is added, the temperature is cooled to 0° C., stirring is conducted for 30 minutes, trimethylsilyl trifluoromethanesulfonate (0.3 μL) is dropwise added, and stirring is conducted for reaction for 8 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→3:2) to obtain a syrup 40 (13.8 mg, 0.005 mmol, 69%). $R_f$=0.65 (PE:EA=1:1). $^1$H NMR (600 MHz, CDCl$_3$) δ: 8.35~7.10 (m, 65H, Ph), 5.60 (s, 1H, Rha2 h-H), 5.57 (s, 1H, Ph-CH), 5.57 (s, 1H, Ph-CH), 5.56 (s, 1H, Ph-CH), 5.48 (m, 3H, Rha2-H), 5.43~5.37 (m, 3H, Man2-H), 5.30 (d, J=1.9 Hz, 1H, Man1-H), 5.29 (d, J=1.4 Hz, 1H, Man1-H), 5.26 (d, J=1.5 Hz, 1H, Man1-H), 5.17 (d, J=20.03 Hz, 3H, Ph-CH2), 4.90~4.10 (m, 33H, Rha1-H, Ph-CH2), 4.05~3.57 (m, 26H), 3.50~3.10 (m, 10H, Rha5-H, linker-NCH$_2$), 2.12 (s, 3H, OAc), 2.10 (s, 6H, OAc), 2.09 (s, 6H, OAc), 2.07 (s, 3H, OAc), 2.03 (s, 3H, OAc), 2.03 (s, 3H, OAc), 1.63~1.45 (m, 4H, linker-CH2), 1.43~1.33 (m, 12H, Rha6-H), 1.33~1.18 (m, 2H, linker-CH2); $^{13}$C NMR (151 MHz, CDCl$_3$) δ: 192.5, 170.8, 170.7, 170.6, 170.1, 170.1, 170.1, 138.9, 138.9, 138.6, 138.6, 138.1, 137.5, 137.5, 137.1, 137.0, 134.6, 129.9, 129.1, 129.1, 129.0, 129.0, 128.9, 128.8, 128.8, 128.7, 128.7, 128.6, 128.6, 128.5, 128.5, 128.4, 128.4, 128.3, 128.3, 128.2, 128.1, 128.1, 128.1, 128.0, 128.0, 127.8, 127.8, 127.7, 127.7, 127.5, 127.5, 127.3, 127.2, 126.2, 126.2, 126.1, 101.6, 101.5, 101.4, 100.4, 100.3, 100.2, 100.0, 98.8, 96.1, 96.0, 95.9, 80.3, 80.2, 79.9, 79.7, 79.6, 78.7, 77.8, 77.7, 76.1, 75.3, 75.0, 73.6, 73.0, 72.1, 72.0, 71.8, 71.7, 71.5, 71.2, 71.0, 70.9, 70.9, 70.9, 69.4, 69.0, 68.8, 68.8, 68.6, 68.6, 67.6, 67.3, 64.7, 64.7, 64.7, 50.7, 50.3, 47.2, 46.3, 29.3, 28.0, 27.6, 23.3, 21.1, 21.1, 21.0, 21.0, 21.0, 18.9, 18.7, 18.7, 18.7, 18.7.

Compound 41: under protection of argon, the compound 30 (52.4 mg, 0.068 mmol) and the compound 39 (78.5 mg, 0.034 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (2 mL) is added, iodosuccinimide (17.6 mg, 0.078 mmol) is added, the temperature is cooled to 0° C., stirring is conducted for 30 minutes, trimethylsilyl trifluoromethanesulfonate (1.2 μL) is dropwise added, and stirring is conducted for reaction for 10 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→3:2) to obtain a syrup 41 (56.5 mg, 0.019 mmol, 55%). $R_f$=0.36 (PE:EA=1:1). $^1$H NMR (400 MHz, CDCl$_3$) δ: 8.35~7.05 (m, 62H, Ph), 5.60 (s, 1H, Rha2i-H), 5.58~5.54 (m, 4H, Ph-CH), 5.51 (d, J=2.7 Hz, 1H, Rha2-H), 5.48 (d, J=2.4 Hz, 3H, Rha2-H), 5.43~5.37 (m, 4H, Man2-H), 5.31~5.24 (m, 4H, Man1-H), 5.22~4.28 (m, 21H, Rha1-H, Ph-CH2), 4.26~4.13 (m, 8H, Man3-H, Man6-H), 3.98~3.86 (m, 9H), 3.85~3.70 (m, 6H), 3.69~3.54 (m, 10H, Rha3-H), 3.53~3.11 (m, 11H, Rha5-H, linker-NCH$_2$), 2.13~2.00 (m, 27H, 9OAc), 1.63~1.45 (m, 4H, linker-CH2), 1.43~1.33 (m, 15H, Rha6-H), 1.33~1.18 (m, 2H, linker-CH2).

Compound 42: under protection of argon, the compound 41 (56.5 mg, 0.019 mmol) is dissolved in methylene dichloride (1 mL), deionized water (0.5 mL), 2,3-dichloro-5,6-dicyan-1, 4-benzoquinone (DDQ) (6.3 mg, 0.028 mmol) are dropwise added in sequence, and stirring is conducted for reaction for 9 hours at the room temperature. After complete reaction of raw materials is monitored by TLC, extraction with methylene dichloride is conducted, washing with a 10% (w/w) sodium thiosulfate solution is conducted, organic phases are collected, drying with anhydrous sodium sulfate is conducted, sodium sulfate is filtered out by using filter paper, a solvent is removed through rotary evaporation, and a crude product is purified by silica gel column chromatography (PE:EA=20:1→3:2) to obtain a brown syrup 42 (27.7 mg, 0.01 mmol, 53%). $R_f$=0.36 (PE:EA=1:1). $^1$H NMR (400 MHz, CDCl$_3$) δ: 7.55~7.10 (m, 55H, Ph), 5.60 (s, 1H, Rha2i-H), 5.58~5.54 (m, 4H, Ph-CH), 5.49 (d, J=2.6 Hz, 4H, Rha2-H), 5.40 (dq, J=3.8, 1.8 Hz, 4H, Man2-H), 5.28 (t, J=2.0 Hz, 2H, Man1-H), 5.26 (d, J=1.6 Hz, 2H, Man1-H), 5.17 (d, J=10.3 Hz, 2H, Ph-CH2), 4.78~4.61 (m, 9H, Rha1-H, Ph-CH2), 4.54~4.27 (m, 9H, Rha1-H, Ph-CH2), 4.26~4.11 (m, 8H, Man3-H, Man6-H), 3.96~3.86 (m, 8H), 3.85~3.70 (m, 6H), 3.69~3.54 (m, 8H, Rha3-H), 3.53~3.11 (m, 11H, Rha5-H, linker-NCH$_2$), 2.13~2.00 (m, 27H, 9OAc), 1.63~1.45 (m, 4H, linker-CH2), 1.43~1.33 (m, 15H, Rha6-H), 1.33~1.18 (m, 2H, linker-CH2).

Compound 2: under protection of argon, the compound 42 (27.7 mg, 0.009 mmol) and the compound 3 (26.3 mg, 0.045 mmol) are dissolved with methylbenzene, water is removed through rotary evaporation three times, the obtained mixture is placed on an oil pump overnight for vacuuming, a pre-activated 4 Å molecular sieve is added, anhydrous methylene dichloride (1 mL) and anhydrous ether (1 mL) are added, iodosuccinimide (10.1 mg, 0.045 mmol) is added, the temperature is cooled to 0° C., stirring is conducted for 30 minutes, trimethylsilyl trifluoromethanesulfonate (0.5 μL) is dropwise added, and stirring is conducted for reaction for 8 hours under an ice bath. After complete reaction of raw materials is monitored by TLC, triethylamine is added for quenching the reaction, diatomaceous earth is added in a sand core funnel, the molecular sieve is filtered out, a solvent is removed through rotary evaporation, and a crude product is purified by silica gel column chromatography (PE:EA=20:1→3:2) to obtain a syrup 2 (21.1 mg, 0.006 mmol, 69%). $R_f$=0.55 (PE:EA=1:1). $^1$H NMR (600 MHz, CDCl$_3$) δ: 7.55~7.10 (m, 75H, Ph), 5.60 (s, 1H, Rha2-H), 5.58~5.54 (m, 4H, Ph-CH), 5.48 (d, J=2.9 Hz, 4H, Rha2-H), 5.40 (m, 4H, Man2-H), 5.29 (t, J=1.8 Hz, 2H, Man1-H), 5.26 (d, J=1.5 Hz, 3H, Man1-H), 5.17 (d, J=12.4 Hz, 2H, Ph-CH2), 4.88~4.58 (m, 14H, Rha1-H, Ph-CH$_2$), 4.55~4.25 (m, 12H, Rha1-H, Ph-CH2), 4.24~4.13 (m, 10H, Man3-H, Man6-H), 4.01 (t, J=9.5 Hz, 1H), 3.96~3.86 (m, 8H), 3.85~3.70 (m, 8H), 3.72~3.53 (m, 12H, Rha3-H), 3.53~3.11 (m, 10H, Rha5-H, linker-NCH$_2$), 2.15~1.98 (m, 27H, 9OAc), 1.63~1.45 (m, 4H, linker-CH2), 1.43~1.32 (m, 15H, Rha6-H), 1.33~1.18 (m, 2H, linker-CH2); $^{13}$C NMR (151 MHz, CDCl$_3$) δ: 192.5, 176.9, 170.7, 170.7, 170.6, 170.1, 170.1, 138.9, 138.9, 138.8, 138.6, 138.5, 138.1, 137.5, 137.1, 137.1, 136.9, 136.6, 134.6, 129.9, 129.1, 129.1, 128.9, 128.9, 128.8, 128.8, 128.7, 128.7, 128.6, 128.6, 128.6, 128.5, 128.5, 128.5, 128.4, 128.4, 128.4, 128.3, 128.3, 128.2, 128.2, 128.1, 128.1, 128.1, 128.0, 128.0, 127.8, 127.7, 127.7, 127.7, 127.6, 127.5, 127.4, 127.2, 126.2, 126.2, 126.1, 101.6, 101.6, 101.4, 100.3, 100.2, 100.0, 98.8, 96.1, 96.0, 95.8, 80.3, 80.2, 79.9, 79.6, 77.9, 77.4, 77.2, 76.9, 76.1, 75.3, 74.9, 73.5, 72.9, 72.6, 72.1, 72.1, 72.1, 72.0, 71.8, 71.6, 71.5, 71.2, 71.0, 70.9, 70.9, 69.8, 69.4, 68.9, 68.8, 68.7, 68.6, 67.6, 67.3, 67.2, 64.7, 50.6, 50.3, 47.2, 29.7, 29.3, 23.3, 21.1, 21.1, 21.0, 21.0, 20.7, 18.9, 18.8, 18.8, 18.7, 18.7, 18.6, 18.6, 18.6.

Compounds 31, 34, 37, 39 and 2 are respectively subjected to deprotection by step b to obtain oligosaccharide fragment compounds 31d, 34d, 37 d, 39d and 2d.

Example 7 Biological Activity of Derivatives of Gram-Positive Bacteria Cell Wall Capsular Polysaccharide:

Culture and Inactivation of *C. bolteae* and Extraction of Capsular Polysaccharides:

During culture of *C. bolteae*, the *C. bolteae* is first cultured at 37° C. under the condition of a gaseous environment of 80% $N_2$ and 10% $CO_2$ in ATCC Medium 1490 (ELITE-MEDIA) for 72 hours to obtain a bacterial solution.

During inactivation of the *C. bolteae,* 5 mL 4% paraformaldehyde is added to a $2\times10^{11}$ CFU/mL, 50 mL bacterial solution to make the final concentration reach 0.4%, and the *C. bolteae* is incubated in the solution at 37° C. for 72 hours. The bacteria were collected centrifugally, washed with PBS (pH 7.4) twice, and finally diluted with PBS (pH 7.4) to $5\times10^{12}$ CFU/mL, and preserved at 4° C.

The *C. bolteae* capsular polysaccharide is extracted through a phenol water method, the bacteria are collected centrifugally, washed twice with a phosphate buffer solution (PBS, pH 7.4), and precipitated, and a wet weight is weighed. A bacteria suspension is obtained through resuspending with sterile water of three times the wet weight of the bacteria, and the bacteria suspension is subjected to repeated freeze-thaw for 5 times. After being mixed with 90% phenol of the same volume and shaken in a constant temperature water bath, the mixture is cooled to 4° C., upper water phases are absorbed centrifugally, then sterile water of the same volume is added, after being shaken in a constant temperature water bath, the mixture is cooled to 4° C., and a supernatant is absorbed centrifugally. The supernatants of two times are combined, are dialyzed with distilled water until there is no purple in a ferric chloride test, and are lyophilized and preserved.

Lyophilized CPS powder is dissolved in Tris-HCl (100 mmol, pH 8.0), a final concentration of 100 μg/ml DNase I and 50 μg/ml RNase A are added, after digestion at 37° C. overnight, 100 μg/ml protease K is added, after action for 2 h, the enzyme is inactivated by boiling with boiling water at 100° C. for 10 min, the solution is cooled to 4° C., and a supernatant is collected centrifugally. Water-saturated phenol is added into the supernatant and is uniformly mixed, a supernatant is collected centrifugally again for dialysis and lyophilization. Anhydrous ethanol is added into the lyophilized powder until the final concentration reaches 85%, and the powder is precipitated overnight at −20° C. After centrifugation, a supernatant is discarded, and precipitation is lyophilized and weighed. Through $H^1$ nuclear magnetic resonance detection, the obtained lyophilized powder has characteristic peaks of the polysaccharide, such as a rhamnose (Rha) C6 site characteristic peak at the chemical shift of 1.34, a hydrogen (α-Man) characteristic peak at a mannose C1 site at the chemical shift of 5.3, and a hydrogen (β-Rha) characteristic peak at a rhamnose C1 site at the chemical shift of 4.90. The extracted capsular polysaccharide is good in visible purity through SDS-PAGE electrophoresis and silver staining (FIGS. 8 and 9), and an average molecular weight of the capsular polysaccharide is mostly distributed at 14.3 KDa or below.

Immunological experiment of *C. bolteae* capsular polysaccharides:

New Zealand rabbits of 1.8 to 2.2 kg are divided into two groups: an experimental group of four and a control group of four. On day 0, New Zealand rabbits in the experimental group I are immunized in subcutaneous multipoints with a 500 μL mixed emulsion of capsular polysaccharide and Freund's complete adjuvant in the ratio of 1:1. New Zealand rabbits in the control group are injected with a 500 μL mixed emulsion of PBS and Freund's complete adjuvant in the ratio of 1:1. On days 14 and 28, a Freund's incomplete adjuvant is used to replace the Freund's complete adjuvant to enhance immunity. Each New Zealand rabbit in the experimental group I is injected with concentration of antigen equivalent to 400 μg of capsular polysaccharide antigen per injection. Serum of the New Zealand rabbits on day 35 is collected for ELISA.

ELISA of *C. bolteae* capsular polysaccharide antiserum:

LPS is diluted to 20 μg/mL with a 0.05 M CBS buffer solution (pH 9.6), then coated with ELISA well plates of 100 L/well at 4° C. for 24 h, washed with PBST (PBS containing 0.1% tween-20) for three times, and patted to be dried. A sealing solution (PBS containing 5% skimmed milk) is added to the coated ELISA plate according to the amount of 300 μL/well, and the plate is sealed by a plate sealing film at 25° C. for 6 h. The sealing solution is discarded, and washing with PBST three times and pat drying are conducted. 100 μL/well, through 1% BSA-PBS (w/v) diluted rabbit serum of different gradients, is added to the coated well plate. Incubation is conducted at 37° C. for 2 h, and washing with PBST four times and pat drying are conducted. Incubation is conducted with goat anti-rabbit secondary antibodies labeled with 1:50,000 diluted horseradish peroxidase at 100 μL/well for 1 h at 37° C., and washing with PBST four times and pat drying are conducted. Incubation is conducted with 200 μL/well TMB color liquid away from light at 37° C., and immediate termination is conducted with 50 μL/well 2 M $H_2SO_4$ after developing. Absorbance at 450 nm is determined. Antibody titers are obtained as shown in FIG. 5. The rabbit serum with the highest antibody titer is selected for carbohydrate chip screening. In ELISA, we found that the serum of New Zealand rabbits injected with *C. bolteae* capsular polysaccharide CPS can bind to the extracted CPS, and effective titers of antibodies in the serum reach 1:10,000 or above.

Application of an Oligosaccharide Compound in Preparation of *C. bolteae* Vaccine:

Preparation of the Oligosaccharide Compound and a CRM-197 Glycoprotein Conjugate:

Triethylamine (12 μL, 86 μmol) is added into a DMSO/pyridine solution (1:1, 25 mL: 0.25 mL) of bis(p-nitrophenyl adipate) (PNP, 26.33 mg, 67.8 mol), and stirring is conducted for 5 minutes at the room temperature. An oligosaccharide compound (1.6 mg, 2.26 mol) dissolved in DMSO/pyridine (1/1, 0.1 mL: 0.1 mL) is dropwise added, stirring is conducted for 7 h at the room temperature, Complete reaction of raw materials is monitored by TLC, sugar stain (0.1% (v/v) 3-methoxyphenol, 2.5% (v/v) sulfuric acid-ethanol) shows products. The reaction mixture is lyophilized. A lyophilized solid is washed six times with chloroform (1 mL) to obtain oligosaccharide-PNP ester. $CRM_{197}$ protein (1 mg, 0.017 μmol) was washed three times with sterilized water (400 μL) and then washed once with a phosphate solution (pH 8.0, 400 μL) in an ultrafiltration device. The cleaned $CRM_{197}$ protein is added to oligosaccharide-PNP ester, stirring is conducted for 24 hours at the room temperature, and then the mixture after reaction is washed with sterilized water and phosphate solutions to obtain the glycoprotein conjugate. The glycoprotein conjugate is identified using MALDI-TOF/TOF-MS and SDS-PAGE.

Glycoconjugate immunological experiment: eight six-week-old Balb/c mice are divided into two groups: an experimental group of five and a control group of three. On day 0, mice in the experimental group are immunized in subcutaneous multipoints with a 100 μL mixed emulsion of glycoconjugate and Freund's complete adjuvant in the ratio of 1:1. Mice in the control group are injected with a 100 μL mixed emulsion of PBS and Freund's complete adjuvant in the ratio of 1:1. On days 14 and 28, a Freund's incomplete adjuvant is used to replace the Freund's complete adjuvant to enhance immunity. Each mouse in the experimental group is injected with concentration of antigen equivalent to 4 μg of carbohydrate antigens. Serum of the mice on days 0, 7, 14, 21 and 35 is collected for chip inspection.

Construction and Testing of Oligosaccharide Chips:

Chemically synthesized oligosaccharide antigens are fixed on the chip surface through aminolinks, and antiserum is incubated with the oligosaccharide chip, and then incubated with secondary antibodies.

Fluorescence of oligosaccharide fragments binding to the antibodies can be obtained under a chip scanner. By this method, the binding strength of the oligosaccharide fragments and the antibodies in serum can be quantified, the amount of chemically synthesized oligosaccharides and the antiserum can be saved, and a result can be clearly reflected.

Assay Process of Antibodies in Antiserum During Immunogenicity Studies Using Oligosaccharide Chips:

The process specifically includes the following steps:

(1) an activated amino slide is subjected to sample application with a biochip arrayer. After sample application, the amino slide is incubated overnight under the conditions of 26° C. and 55% humidity.

(2) Then the slide is soaked in a solution B (an aqueous solution of 50 nM $Na_2HPO_4$ and 100 nM ethanolamine) at 50° C. for 1 h. The slide is washed with ultrapure water three times and centrifuged to remove the residual water.

(3) The slide is sealed overnight at 4° C. with a 3% BSA (w/w) PBS solution. Then the slide is washed with PBST (PBS containing 0.1% tween) once, washed with PBS twice, and spin-dried centrifugally.

(4) The slide is loaded into a 16-well incubator (ProPlate). Mice serum samples of 120 μL diluted in a 1% BSA (w/v) PBS solution in the ratio of 1:50 are added to each well and incubated in a wet box at 37° C. away from light for 1 hour. The samples are removed, and are washed with 150 μL PBST three times.

(5) The secondary antibodies diluted in a 1% BSA (w/v) PBS solution in the ratio of 1:400 are added, and are incubated in a wet box at 37° C. away from light for 45 minutes. A secondary antibody solution is removed, and washed with 150 μL PBST three times. The 16-well incubator is removed, washed with ultrapure water, and then washed with ultrapure water for 15 minutes. Residual water is removed through centrifugation. The obtained product is scanned with a chip scanner.

Immunogenicity Assay of Oligosaccharide Fragments Synthesized by *C. bolteae* Capsular Polysaccharides:

An NHS slide (SurModics, DN01-0025) is subjected to sample application with a biochip arrayer (Jiangsu Ruiming Biotechnology Co., LTD.). After sample application, the NHS slide is incubated overnight under the conditions of 26° C. and 55% humidity. Then the slide is soaked in a solution B (an aqueous solution of 50 nM $Na_2HPO_4$ and 100 nM ethanolamine) at 50° C. for 1 h. The slide is washed with ultrapure water three times and centrifuged to remove the residual water. The slide is sealed overnight at 4° C. with a 3% BSA (w/w) PBS solution. The slide is washed with PBST (PBS containing 0.1% tween) once, washed with PBS twice, and spin-dried centrifugally. The slide is loaded into a 16-well incubator (ProPlate). Mice serum samples of 120 μL diluted in a 1% BSA (w/v) PBS solution in the ratio of 1:50 are added to each well and incubated in a wet box at 37° C. away from light for 1 hour. The samples are removed, and washed with 150 μL PBST three times, the secondary antibodies diluted in a 1% BSA (w/v) PBS solution in the ratio of 1:400 are added, and is incubated in a wet box at 37° C. away from light for 45 minutes. A secondary antibody solution is removed, and washed with 150 μL PBST three times. The 16-well incubator is removed, washed with ultrapure water, and then washed with ultrapure water for 15 minutes. Residual water is removed through centrifugation. The obtained product is scanned with a chip scanner. Results are obtained: the antiserum and extracted capsular polysaccharides can be strongly bound, and in all oligosaccharide fragments, disaccharide 31d and tetrose 34d fragments are relatively strong in fluorescence intensity, especially the binding of tetrose 34d to the antiserum is strongest, it may be concluded that the disaccharide and the tetrose, especially tetrose fragments are important immune epitopes, and may be used as an important antigen substance of semisynthetic carbohydrate vaccine.

The present disclosure uses a chemical method to synthesize *C. bolteae* capsular polysaccharide antigens and carbohydrate chips thereof, completes chemical synthesis of *C. bolteae* surface capsular polysaccharide assembled with orthogonal linkers [→3)-α-D-Manp-(1→4)-3-D-Rhap-(1→]9-Linker for the first time, and fixes the synthetic oligosaccharide on the surface of the chip through an aminolink to prepare a synthetic oligosaccharide chip. At the same time, biologically extracted capsular polysaccharides are used to stimulate experimental animals to generate specific antiserum, and the antiserum can be used to analyse the polysaccharide antigens through the synthetic carbohydrate chip, wherein the disaccharide and the tetrose have good binding with specific antiserum generated by the animals, and the tetrose fragments may be used as carbohydrate antigen fragments for preparation and development of *C. bolteae* prevention and treatment vaccine.

Although the present disclosure has been disclosed in an exemplary example as mentioned above, it is not intended to define the present disclosure. Anyone familiar with the technology can make various alterations and modifications without departing from the spirit and scope of the present disclosure. Therefore, the protection scope of the present disclosure shall be as defined in the claims.

What is claimed is:

1. A gram-positive bacteria cell wall capsular polysaccharide compound, comprising one or more of a disaccharide, a trisaccharide, a tetrasaccharide, a pentaose, a hexaose, a heptaose, an octaose, a nonose and a decose:

wherein a structure of the decose is shown in formula I:

Formula I wherein $R_6$ is an aminolink [—(CH2)$_n$—N—$Y_1Y_2$, n=1 to 10], and is used to be linked with a protein, n represents that the aminolink has different carbon chain lengths, $Y_1$ and $Y_2$ are protecting groups for amino, and independently selected from H, benzyl (Bn), or benzyloxycarbonyl (Cbz); wherein $R_2$, $R_3$, $R_4$ and $R_5$ groups are independently selected from H, acetyl (Ac), benzoyl (Bz), pivalyl (Piv), chloracetyl (ClAc), levulinic acyl (Lev), allyloxycarbonyl (Alloc), benzyl (Bn), 2-menaphthyl (Nap), allyl (All), benzylidene acetal or isopropylidene ketal;

wherein $R_7$ and $R_{12}$ groups are independently selected from H, acetyl (Ac), benzoyl (Bz), pivalyl (Piv), chloracetyl (ClAc), levulinic acyl (Lev) or allyloxycarbonyl (Alloc), and $R_8$ is H, benzyl (Bn) or allyl (All); and wherein $R_{13}$ and $R_{14}$ are independently selected from H, benzyl (Bn), 2-menaphthyl (Nap), allyl (All), benzylidene acetal or isopropylidene ketal;

wherein the disaccharide is shown in the following formula:

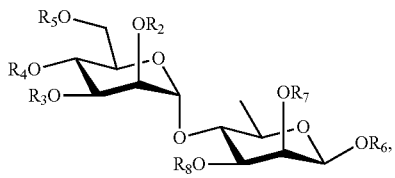

wherein $R_2$, $R_3$, $R_4$, $R_5$, $R_6$, $R_7$ and $R_8$ refer to formula I;

the trisaccharide is shown in the following formula:

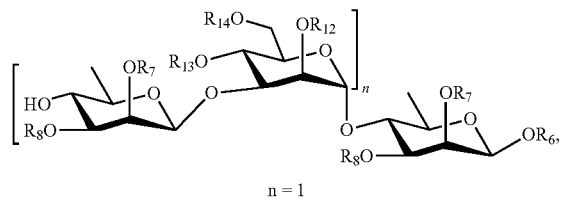

n = 1 wherein $R_{12}$, $R_{13}$, $R_{14}$, $R_6$, $R_7$ and $R_8$ refer to formula I;

the tetrasaccharide is shown in the following formula:

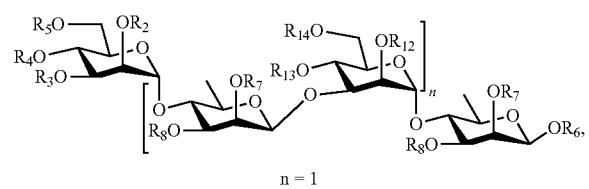

n = 1 wherein $R_2$, $R_3$, $R_4$, $R_5$, $R_6$, $R_7$, $R_8$, $R_{12}$, $R_{13}$ and $R_{14}$ refer to formula I;

the pentaose is shown in the following formula:

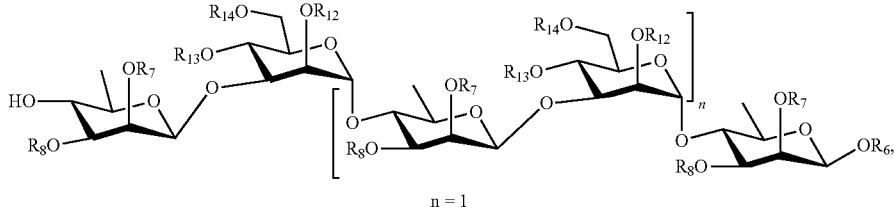

n = 1 wherein $R_6$, $R_7$, $R_8$, $R_{12}$, $R_{13}$ and $R_{14}$ refer to formula I;

the hexaose is shown in the following formula:

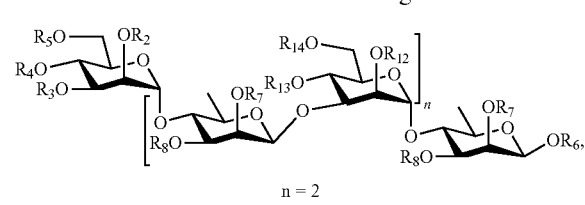

n = 2 wherein $R_2$, $R_3$, $R_4$, $R_5$, $R_{12}$, $R_{13}$, $R_{14}$, $R_6$, $R_7$ and $R_8$ refer to formula I;

the heptaose is shown in the following formula,

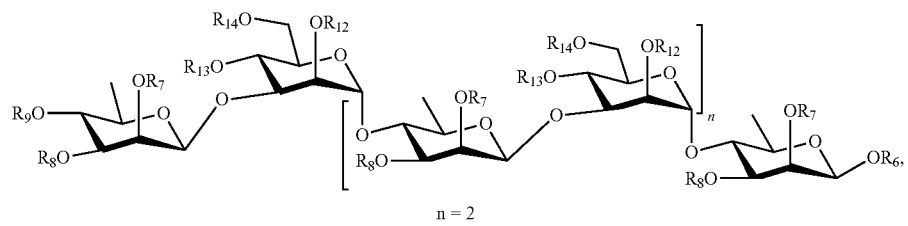

n = 2 wherein $R_{12}$, $R_{13}$, $R_{14}$, $R_6$, $R_7$, $R_8$ and $R_9$ refer to formula I; and $R_9$ groups is H, acetyl (Ac), benzoyl (Bz), pivalyl (Piv), chloroacetyl (ClAc), levulinic acyl (Lev), allyloxycarbonyl (Alloc), benzyl (Bn), 2-menaphthyl (Nap), p-Methoxybenzyl (pMBn), allyl (All), benzylidene acetal or isopropylidene ketal;

the octaose is shown in the following formula:

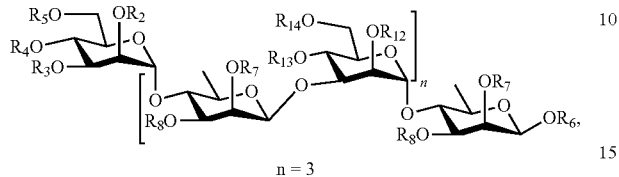

n = 3 wherein $R_2$, $R_3$, $R_4$, $R_5$, $R_{12}$, $R_{13}$, $R_{14}$, $R_6$, $R_7$ and $R_8$ refer to formula I; and the nonose is shown in the following formula:

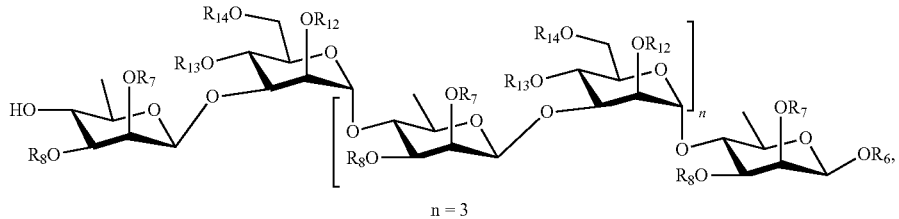

n = 3 wherein $R_{12}$, $R_{13}$, $R_{14}$, $R_6$, $R_7$ and $R_8$ refer to formula I.

2. A method for synthesizing the gram-positive bacteria cell wall capsular polysaccharide compound of claim 1, comprising the following synthesizing route:

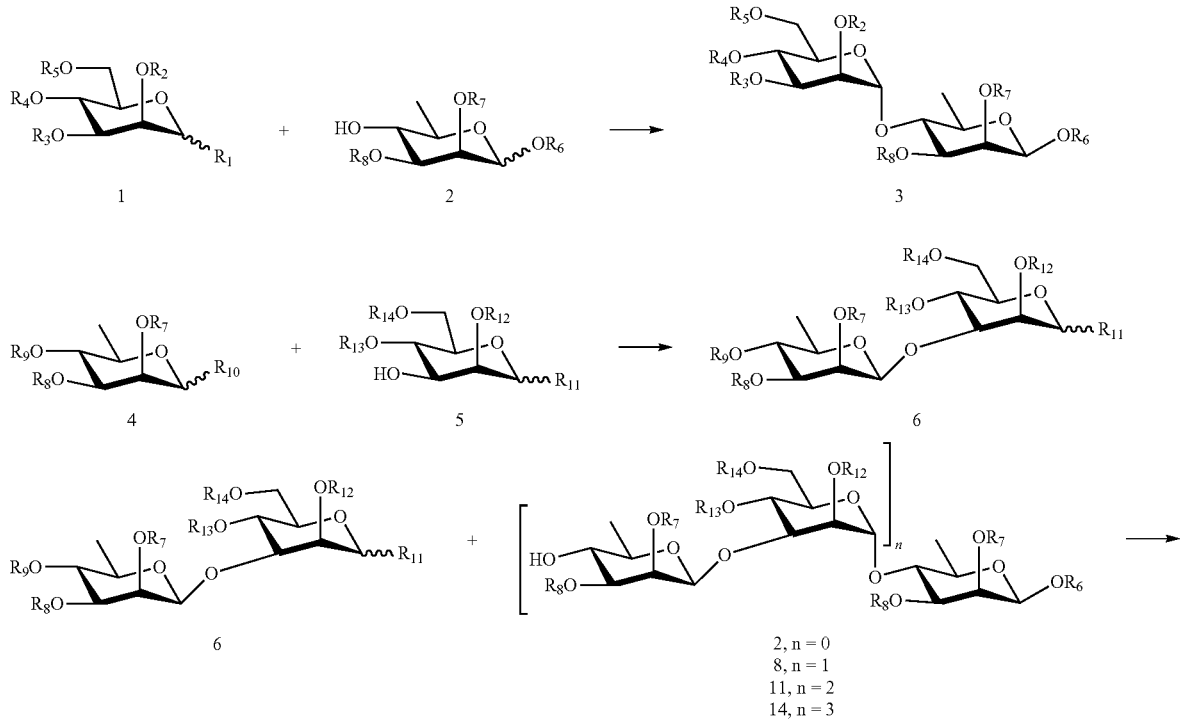

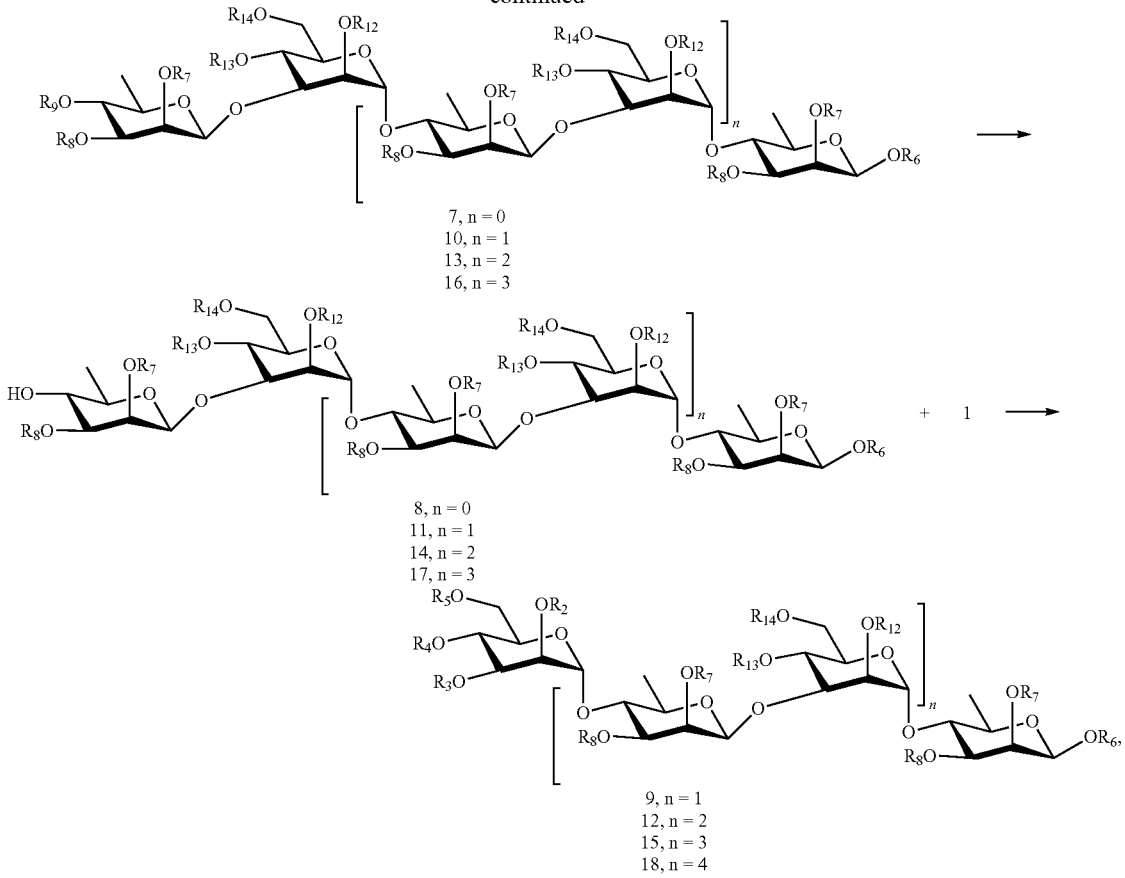

7, n = 0
10, n = 1
13, n = 2
16, n = 3

8, n = 0
11, n = 1
14, n = 2
17, n = 3

9, n = 1
12, n = 2
15, n = 3
18, n = 4 wherein $R_2$, $R_3$, $R_4$, $R_5$, $R_{12}$, $R_{13}$ and $R_{14}$ groups are separately and independently selected from ester protecting groups, ether protecting groups and acetal and ketal protecting groups; $R_6$ is an aminolink; $R_7$, $R_8$ and $R_9$ groups are H, acetyl (Ac), benzoyl (Bz), pivalyl (Piv), chloroacetyl (ClAc), levulinic acyl (Lev), allyloxycarbonyl (Alloc), benzyl (Bn), 2-menaphthyl (Nap), p-Methoxybenzyl (pMBn), allyl (All), benzylidene acetal or isopropylidene ketal; $R_1$, $R_{10}$ and $R_{11}$ are glycosyl donors, and independently selected from halogenated sugars, glucosinolates, trichloroacetimidate glycosides, phosphate glycosides, sulfoxide glycosides or N-phenyl trifluoroacetimidate glycosides.

3. The method according to claim 2, wherein the synthesizing the gram-positive bacteria cell wall capsular polysaccharide compound comprises the following steps:
taking carbohydrate building block 1 as a glycosyl donor, taking carbohydrate building block 2 as a glycosyl receptor, dissolving the glycosyl donor and the glycosyl receptor in dry methylene dichloride, adding a molecular sieve, then performing lewis acid catalysis, and stirring at a certain temperature for reaction for 2 to 10 hours to prepare 1,4-α-linked disaccharide fragment 3.

4. The method according to claim 3, further comprising taking carbohydrate building block 4 as a glycosyl donor, taking carbohydrate building block 5 as a glycosyl receptor, dissolving the glycosyl donor and the glycosyl receptor in dry methylene dichloride, adding a molecular sieve, then performing lewis acid catalysis, and stirring at a certain temperature for reaction for 2 to 10 hours to prepare 1,3-β-linked disaccharide building block 6.

5. The method according to claim 4, further comprising taking the disaccharide building block 6 as a glycosyl donor, taking the carbohydrate building block 2 as a glycosyl receptor, dissolving the glycosyl donor and the glycosyl receptor in methylene dichloride, then performing lewis acid catalysis, and stirring at a certain temperature for reaction for 2 to 10 hours to prepare trisaccharide fragment 7.

6. The method according to claim 5, further comprising selectively eliminating $R_9$ of the trisaccharide fragment 7 to obtain trisaccharide building block 8 with a free hydroxyl group at the C-4 site, taking the carbohydrate building block 1 as a glycosyl donor, taking the trisaccharide building block 8 as a glycosyl receptor, dissolving the glycosyl donor and the glycosyl receptor in dry methylene dichloride, adding a molecular sieve, then performing lewis acid catalysis, and stirring at a certain temperature for reaction for 2 to 10 hours to prepare tetrasaccharide fragment 9.

7. The method according to claim 6, further comprising taking the disaccharide building block 6 as a glycosyl donor, taking the trisaccharide building block 8 as a glycosyl receptor, dissolving the glycosyl donor and the glycosyl receptor in methylene dichloride, then performing lewis acid catalysis, and stirring at a certain temperature for reaction for 2 to 10 hours to prepare pentaose fragment 10.

8. The method according to claim 7, further comprising selectively eliminating $R_9$ of the pentaose fragment 10 to obtain pentaose building block 11 with a free hydroxyl group at the C-4 site, taking the carbohydrate building block 1 as a glycosyl donor, taking the pentaose building block 11 as a glycosyl receptor, dissolving the glycosyl donor and the glycosyl receptor in dry methylene dichloride, adding a molecular sieve, then performing lewis acid catalysis, and stirring at a certain temperature for reaction for 2 to 10 hours to prepare hexaose fragment 12.

9. The method according to claim 8, further comprising taking the disaccharide building block 6 as a glycosyl donor, taking the pentaose building block 11 as a glycosyl receptor, dissolving the glycosyl donor and the glycosyl receptor in methylene dichloride, then performing lewis acid catalysis, and stirring at a certain temperature for reaction for 2 to 10 hours to prepare heptaose fragment 13.

10. The method according to claim 9, further comprising selectively eliminating $R_9$ of the heptaose fragment 13 to obtain heptaose building block 14 with a free hydroxyl group at the C-4 site, taking the carbohydrate building block 1 as a glycosyl donor, taking the heptaose building block 14 as a glycosyl receptor, dissolving the glycosyl donor and the glycosyl receptor in dry methylene dichloride, adding a molecular sieve, then performing lewis acid catalysis, and stirring at a certain temperature for reaction for 2 to 10 hours to prepare octaose fragment 15.

11. The method according to claim 10, further comprising taking the disaccharide building block 6 as a glycosyl donor, taking the heptaose building block 14 as a glycosyl receptor, dissolving the glycosyl donor and the glycosyl receptor in methylene dichloride, then performing lewis acid catalysis, and stirring at a certain temperature for reaction for 2 to 10 hours to prepare nonose fragment 16.

12. The method according to claim 11, further comprising selectively eliminating $R_9$ of the nonose fragment 16 to obtain nonose building block 17 with a free hydroxyl group at the C-4 site, taking the carbohydrate building block 1 as a glycosyl donor, taking the nonose building block 17 as a glycosyl receptor, dissolving the glycosyl donor and the glycosyl receptor in dry methylene dichloride, adding a molecular sieve, then performing lewis acid catalysis, and stirring at a certain temperature for reaction for 2 to 10 hours to prepare target decose fragment 18.

13. The method according to claim 2, wherein when preparing the glycosyl donors 1 and 6, the glycosyl donor is halogenated sugars, glucosinolates, trichloroacetimidate glycosides, phosphate glycosides, sulfoxide glycosides or N-phenyl trifluoroacetimidate glycosides, wherein the $R_1$ group and the $R_{11}$ group are separately and independently selected from hydrogen (H), fluorine (F), chlorine (Cl), bromine (Br), iodine (I), trichloroacetimidate ($CCl_3C$(=NH)O—), N-phenyl trifluoroacetimidate glycosides ($CF_3C$(=NPh)O—), ethyl sulfenyl (SEt), thiophenyl (SPh), paratoluene sulfenyl (STol), ethyl sulfenyl (SEt) or dibutyl phosphonic acid groups (—P(=O)—$(OBu)_2$).

14. The method according to claim 13, wherein the $R_2$, $R_3$, $R_4$ and $R_5$ groups are separately and independently selected from hydrogen (H), acetyl (Ac), benzoyl (Bz), pivalyl (Piv), chloroacetyl (ClAc), levulinic acyl (Lev), allyloxycarbonyl (Alloc), benzyl (Bn), 2-menaphthyl (Nap), p-Methoxybenzyl (pMBn), allyl (All), benzylidene acetal or isopropylidene ketal.

15. The method according to claim 3, wherein $R_6$ of the carbohydrate building block 2 is an aminolink [—$(CH_2)_n$—N—$Y_1Y_2$, n=1 to 10], and is used to be linked with a protein, n represents that the aminolink has different carbon chain lengths, the aminolink is linked through α or β, $Y_1$ and $Y_2$ are protecting groups for amino, and independently selected from H, benzyl (Bn), or benzyloxycarbonyl (Cbz).

16. The method according to claim 3, wherein the lewis acid is boron trifluoride diethyl etherate, trifluoromethanesulfonic acid, trimethylsilyl trifluoromethanesulfonate, silver carbonate or silver trifluoromethanesulfonate.

17. The method according to claim 3, wherein stirring at the certain temperature means ice-bath stirring at room temperature of 25° C., stirring in a mixture of ice and salt at −5° C. to −20° C., stirring in a mixture of acetonitrile and dry ice at −40° C., or stirring in a mixture of acetone and dry ice at −78° C.

* * * * *